US008084584B2

(12) United States Patent
Sugo et al.

(10) Patent No.: US 8,084,584 B2
(45) Date of Patent: Dec. 27, 2011

(54) METHODS FOR STABILIZING PROTEINS

(75) Inventors: Izumi Sugo, Shizuoka (JP); Kikuo Tomonou, Shizuoka (JP)

(73) Assignee: Chugai Seiyaku Kabushiki Kaisha (JP)

( * ) Notice: Subject to any disclaimer, the term of this patent is extended or adjusted under 35 U.S.C. 154(b) by 519 days.

(21) Appl. No.: 11/508,070

(22) Filed: Aug. 22, 2006

(65) Prior Publication Data

US 2006/0287508 A1 Dec. 21, 2006

Related U.S. Application Data

(63) Continuation of application No. 10/500,184, filed as application No. PCT/JP02/013804 on Dec. 27, 2002, now abandoned.

(30) Foreign Application Priority Data

Dec. 28, 2001 (JP) ................................ 2001-400895

(51) Int. Cl.
*A61K 39/395* (2006.01)
*C07K 16/00* (2006.01)

(52) U.S. Cl. ................ 530/387.3; 435/69.1; 435/320.1; 435/326

(58) Field of Classification Search ........................ None
See application file for complete search history.

(56) References Cited

U.S. PATENT DOCUMENTS 5,994,511 A 11/1999 Lowman et al.
6,172,213 B1 1/2001 Lowman et al.
2004/0044187 A1 3/2004 Sato et al.

FOREIGN PATENT DOCUMENTS

EP 1069185 A1 1/2001
WO WO 99/51743 10/1999

OTHER PUBLICATIONS

Geiger et al., J. of Biol. Chem. 1987, vol. 262, p. 785-794.*

Sugo et al., "Study on Structural Properties of Antibody Pharmaceuticals (3)—Activity Reduction Cause by Deamidation of Asn Residues and Molecular Design for Preventing the Reduction," Proc. 124$^{th}$ Ann. Meeting Pharmacol. Soc. Japan (Nihon Yakugakukai Dai124nenkai Osaka 2004 youshisyu), 30[p2]III-386, p. 103 (Mar. 5, 2004) (Translation included).

Bischoff and Kolbe, "Deamidation of Asparagine and Glutamine Residues in Proteins and Peptides: Structural Determinants and Analytical Methodology," *Journal of Chromatography B*, 662:261-278 (1994).

Blanche et al., "Stabilization of Recombinant Adenovirus: Site-Directed Mutagenesis of Key Asparagine Residues in the Hexon Protein," *Analytical Biochemistry*, 297:1-9 (2001).

Cacia et al., "Isomerization of an Aspartic Acid Residue in the Complementarity-Determining Regions of a Recombinant Antibody to Human IgE: Identification and Effect on Binding Affinity," *Biochemistry*, 35:1897-1903 (1996).

Chothia and Lesk, "Canonical Structures for the Hypervariable Regions of Immunoglobulins," *Journal of Molecular Biology*, 196:901-917 (1987).

Chothia et al., "Structural Repertoire of the Human $V_H$ Segments," *Journal of Molecular Biology*, 227:799-817 (1992).

Goolcharran et al. "The Effects of a Histidine Residue on the C-terminal Side of an Asparaginyl Residue on the Rate of Deamidation Using Model Pentapeptides." Journal of Pharmaceutical Sciences 89(6):818-825, Jun. 2000.

Harris et al., "Identification of Multiple Sources of Charge Heterogeneity in a Recombinant Antibody," *Journal of Chromatography B*, 752:233-245 (2001).

Manning et al., "Stability of Protein Pharmaceuticals," Pharm. Res., 6(11):903-918 (1989).

Robinson and Robinson, "Deamidation of Human Proteins," *Proceedings of the National Academy of Sciences USA*, 98:12409-12413 (2001).

Robinson and Robinson, "Molecular Clocks," *Proceedings of the National Academy of Sciences USA*, 98:944-949 (2001).

Scotchler et al., "Deamidation of Glutaminyl Residues: Dependence on pH Temperature, and Ionic Strength," *Analytical Biochemistry*, 59:319-322 (1974).

Tomizawa et al., "Stabilization of Lysozyme Against Irreversible Inactivation by Alterations of the Asp-Gly Sequences," *Protein Engineering*, 8:1023-1028 (1995).

Tyler-Cross et al. "Effects of Amino Acid Sequence, Buffers, and Ionic Strength on the Rate and Mechanism of Deamidation of Asparagine Residues in Small Peptides." Journal of Biological Chemistry 266(33):22549-22556, 1991.

Fish & Richardson P.C., Preliminary Amendment, U.S. Appl. No. 10/500,184, mailed Feb. 28, 2005, 1 page.

Requirement for Restriction/Election, U.S. Appl. No. 10/500,184 mailed Oct. 21, 2005, 5 pages.

Fish & Richardson P.C., Response to Requirement for Restriction/Election, U.S. Appl. No. 10/500,184, mailed Nov. 21, 2005, 8 pages.

Office Action, U.S. Appl. No. 10/500,184 mailed Feb. 22, 2006, 8 pages.

U.S. Patent Office, Notice of Abandonment, U.S. Appl. No. 10/500,184, mailed Oct. 10, 2006, 2 pages.

Chen et al., "Selection and Analysis of an Optimized Anti-VEGF Antibody: Crystal Structure of an Affinity-matured Fab in Complex with Antigen," *J. Mol. Biol.*, 293(4):865-81, Nov. 5, 1999.

* cited by examiner

*Primary Examiner* — Yunsoo Kim
(74) *Attorney, Agent, or Firm* — Fish & Richardson P.C.

(57) ABSTRACT

The present inventors revealed that deamidation of an antibody can be suppressed without influencing its activity by substituting a glycine that is located adjacent to an asparagine with another amino acid.

10 Claims, 17 Drawing Sheets

FIG. 1

HEAVY CHAIN

QVQLLESGAVLARPGTSVKISCKASGFNIK DYYMH WVKQRPGQGLEWIG GNDPANGHSMYDPKFQG

FR1 CDR1 FR2 CDR2

RVTITADTSTSTVFMELSSLRSEDTAVYYCAR DSGYAMDY WGQGTLVTVSS

FR3 CDR3 FR4

ASTKGPSVFPLAPCSRSTSESTAALGCLVKDYFPEPVTVSWNSGALTSGVHTFPAVLQSSGLYSLSSVVTVPSSSLGTKTYTCNVDHKPSNTK
VDKRVESKYGPPCPPCPAPEFLGGPSVFLFPPKPKDTLMISRTPEVTCVVVDVSQEDPEVQFNWYVDGVEVHNAKTKPREEQFNSTYRVVS
VLTVLHQDWLNGKEYKCKVSNKGLPSSIEKTISKAKGQPREPQVYTLPPSQEEMTKNQVSLTCLVKGFYPSDIAVEWESNGQPENNYKTTP
PVLDSDGSFFLYSRLTVDKSRWQEGNVFSCSVMHEALHNHYTQKSLSLSLGK

LIGHT CHAIN

DIQMTQSPSSLSASVGDRVTITCKASQDIKSFLSWYQQKPEKAPKSLIYYATSLADGVPSRFSGSGSGTDYTLTISSLQPEDFATYYCLQHGES
PYTFGGGTKVEIKRTVAAPSVFIFPPSDEQLKSGTASVVCLLNNFYPREAKVQWKVDNALQSGNSQESVTEQDSKDSTYSLSSTLTLSKADY
EKHKVYACEVTHQGLSSPVTKSFNRGEC

FIG. 2
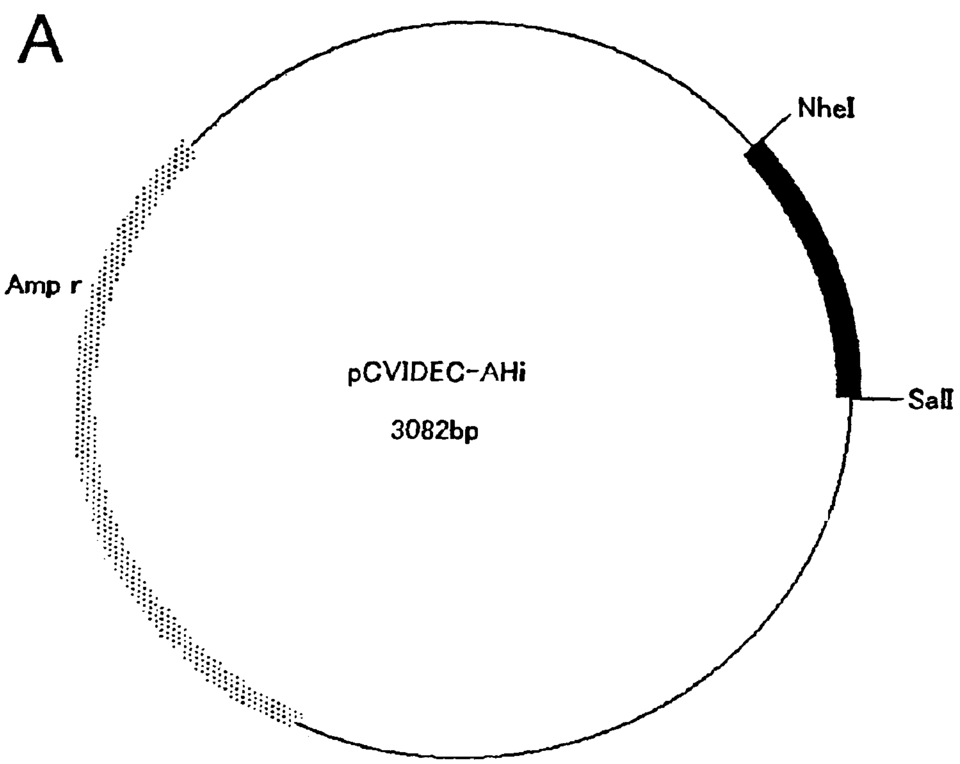
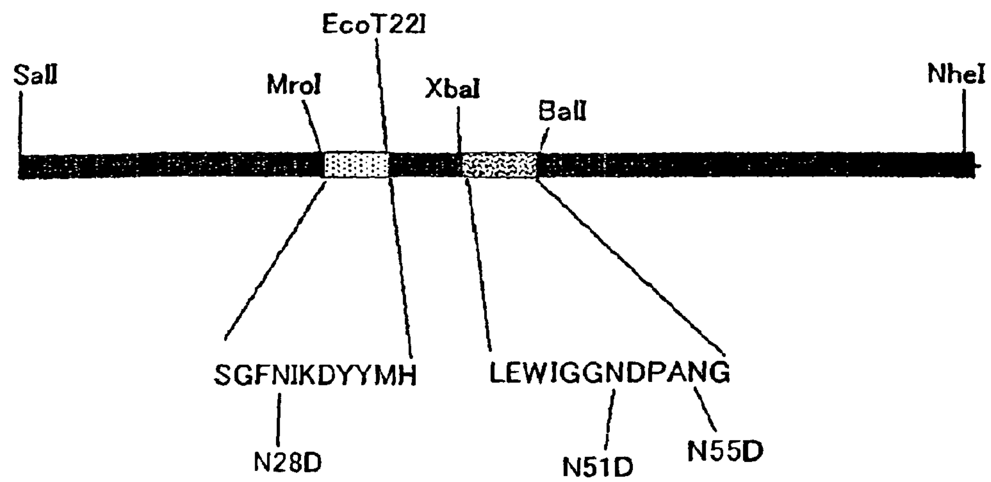

FIG. 3
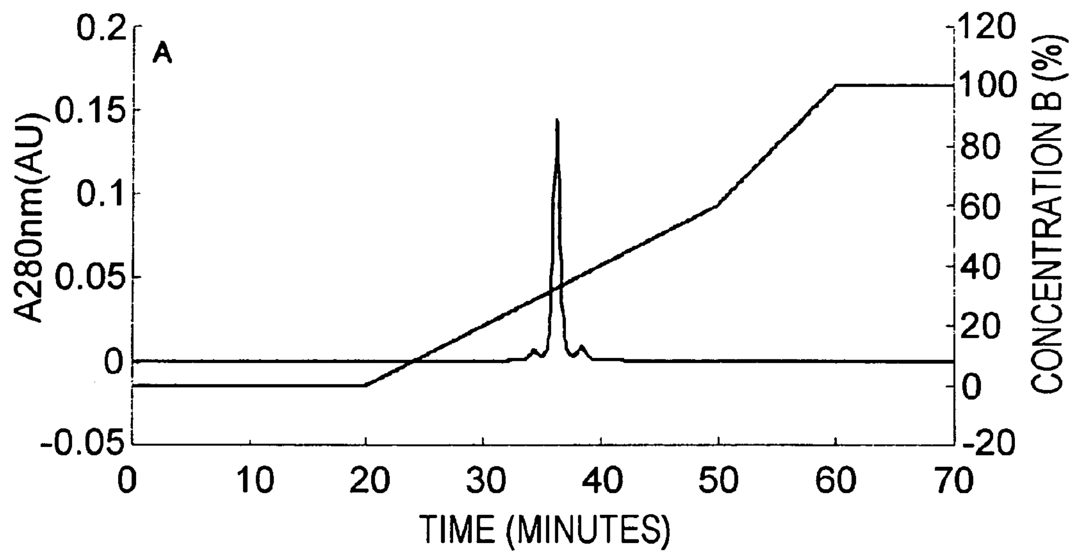
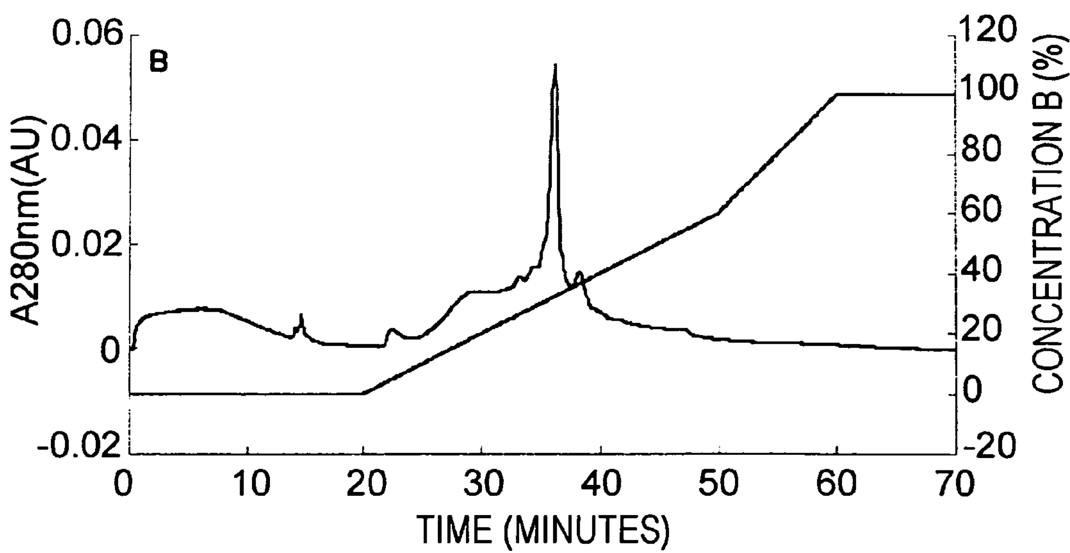

FIG. 4
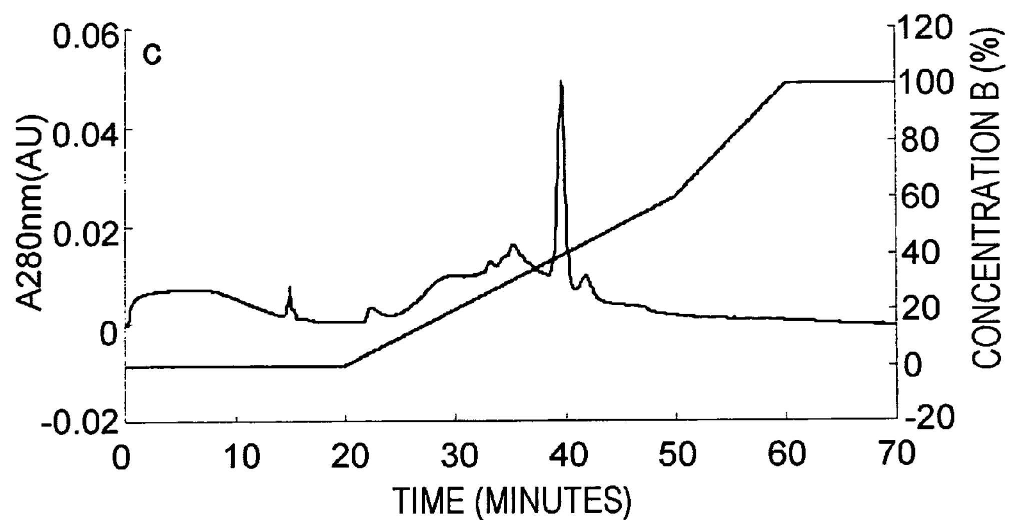
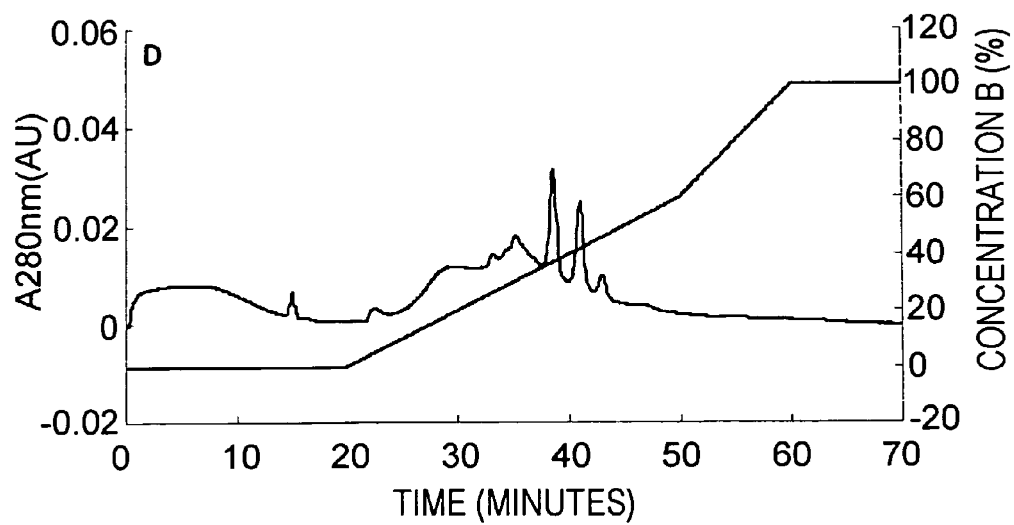

FIG. 5
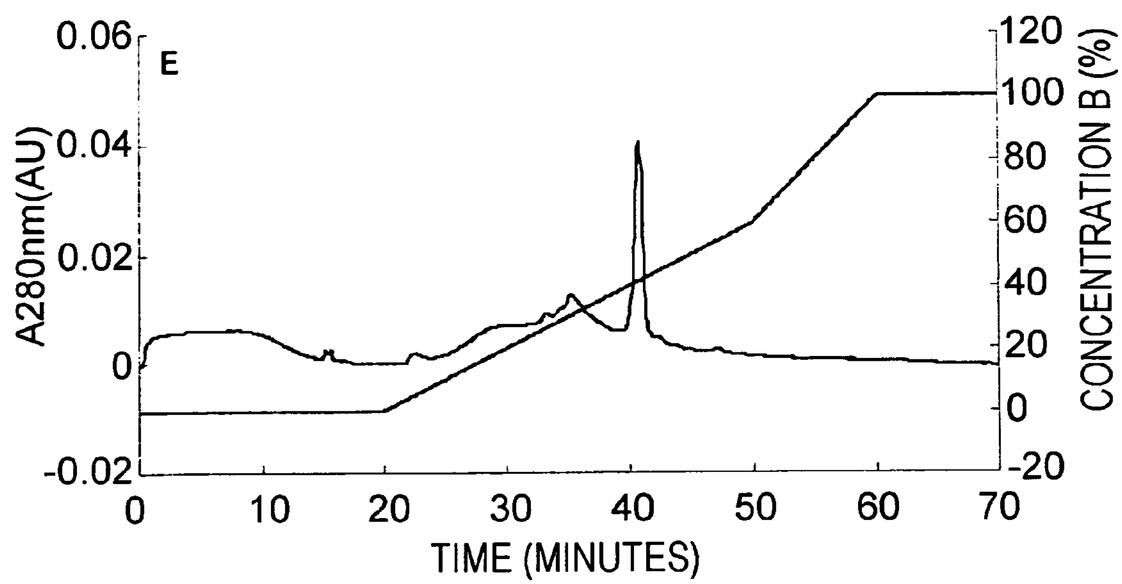
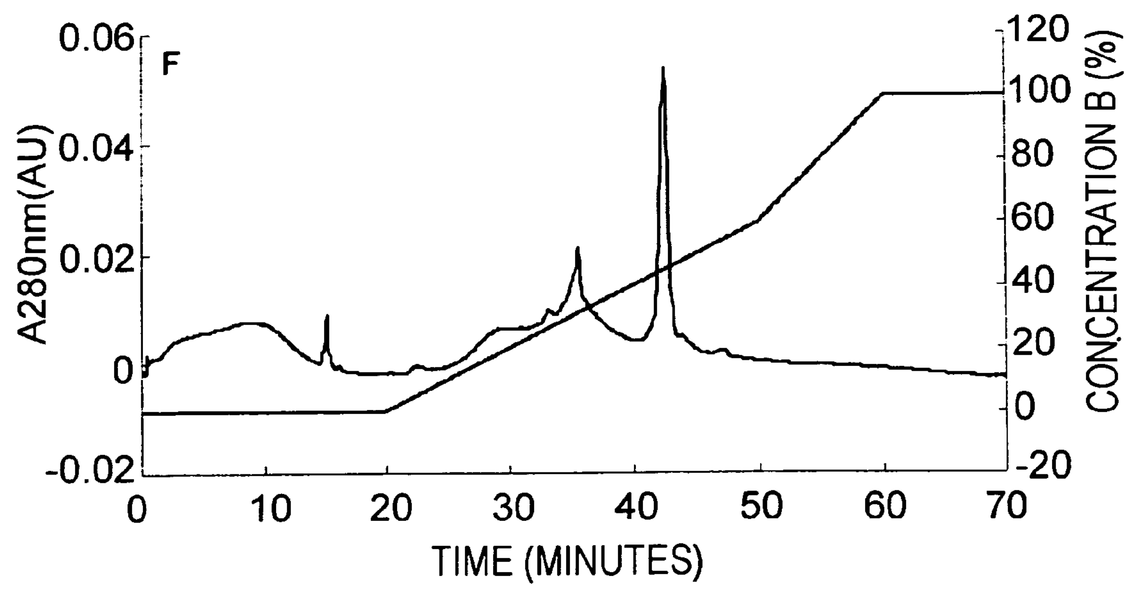

FIG. 9
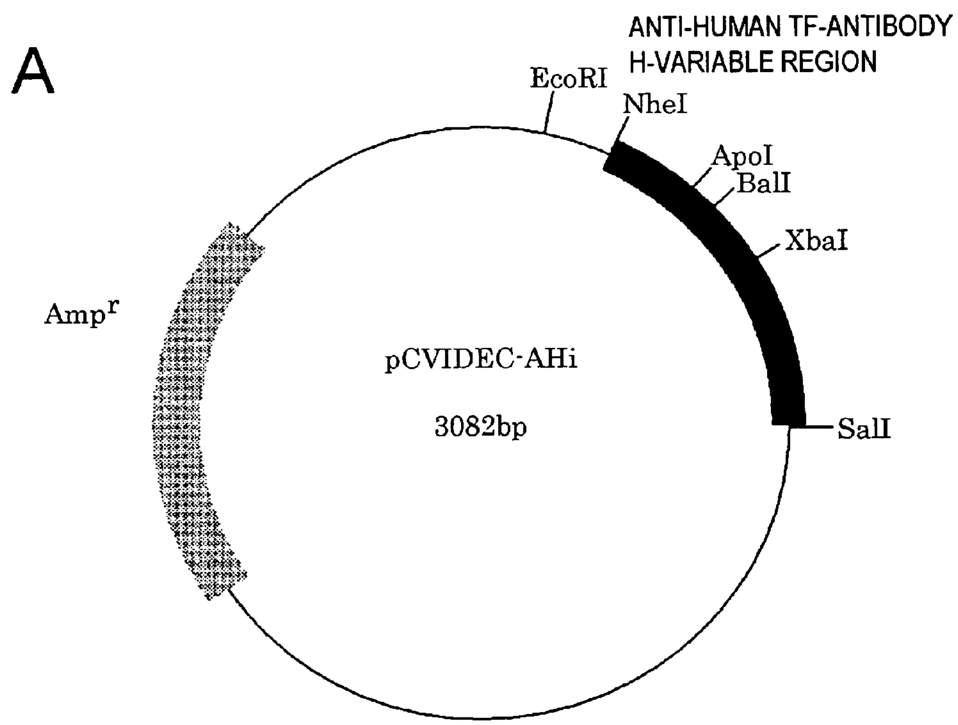
B
5'                                                                 3'
GAGTCTAGAATGGATTGGTGGGAATGATCCTGCGAAT
CTCAGATCTTACCT AACCACCCTT ACTAGGACGCTTANN
3'                                                                 5'
XbaI                                                             BalI
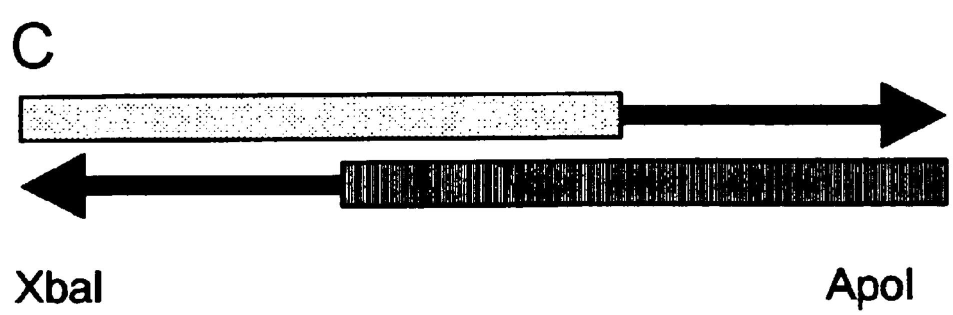

METHODS FOR STABILIZING PROTEINS

CROSS-REFERENCE TO RELATED APPLICATIONS

This application is a continuation of U.S. patent application Ser. No. 10/500,184, filed on Feb. 28, 2005 now abandoned, which is the National Stage of International Application No PCT/JP02/13804, filed Dec. 27, 2002, which claims priority to Japanese Patent Application No. 2001/400895, filed Dec. 28, 2001. The contents of the prior applications are incorporated herein by reference in their entirety.

TECHNICAL FIELD

The present invention relates to methods for improving protein stability. Specifically, the present invention relates to methods for stabilizing proteins comprising the step of substituting an amino acid that is located adjacent to an amino acid being deamidated in a protein with another amino acid.

BACKGROUND ART

Gradual deamidation of amino acids, such as asparagine, in proteins over time can cause a reduction in protein stability. When proteins, particularly antibodies, are used as pharmaceutical agents for various diseases, they are required to be stable over a long period. However, the activity of antibodies decreases with time. The cause for reduction in activity varies in antibodies. Deamidation of amino acids such as asparagine in the antibody is known to be one of the causes.

Therefore, proteins can be stabilized by suppressing deamidation of asparagines. Thus, research on suppressing deamidation of asparagine has been conducted. Substitution of asparagine with another amino acid by site-directed mutagenesis is considered the most certain method to prevent deamidation of proteins. However, such a substitution has the potential to influence protein activity. For example, when the asparagine is located in the complementarity determining region (CDR) of an antibody, such substitution is reported to affect the antibody binding affinity (Presta L. et al., Thromb. Haemost. 85: 379-389, 2001). An anti-human tissue factor (TF) antibody that is expected to inhibit thrombus formation without inhibiting the extrinsic blood coagulation reaction via the inhibition of Factor X activation mediated by TF in the intrinsic blood coagulation reaction is known in the art (WO 99/51743). This antibody has not been formulated as a pharmaceutical preparation, and its activity reduces over time under antibody destabilizing conditions. The deamidation of the anti-human TF antibody is supposed to be a factor in such reduction.

Thus, a method to suppress deamidation of asparagine without influencing antibody activity has been desired in the art.

SUMMARY OF THE INVENTION

Reduction in protein activity is a very important problem from a medical and pharmaceutical perspective. Particularly, antibodies that are stable for a long time and which can be used as pharmaceutical agents are clinically desired. To stabilize antibodies, it can be necessary to suppress deamidation over time of amino acids such as asparagine, especially the asparagines in Asn-Gly containing sequences that are readily deamidated.

Conventionally, methods of suppressing deamidation by altering amino acids in proteins are useful techniques to improve the value and quality of pharmaceuticals. Such methods increase the option in the formulation of pharmaceutical preparations, and thus facilitate application of the proteins in various drug forms and administration routes. Therefore, the purpose of the present invention is to provide a method to suppress deamidation of asparagine without influencing the activity of proteins, particularly antibodies.

The present inventors diligently conducted research focusing on anti-human TF antibody, the use of which as a pharmaceutical is expected in the art. The antibody was used as an example of a protein for developing a method of suppressing deamidation of asparagine without affecting the protein's activity. First, an anti-human TF antibody having an asparagine in a CDR was expressed as a recombinant mutant in which the asparagine was substituted with aspartic acid. The TF binding activity of anti-human TF antibody was hypothesized to decrease significantly due to the deamidation of Asn55 existing in the CDR2 region of the anti-human TF antibody heavy chain (H chain). The amino acid adjacent to Asn55 in the CDR2 region of anti-human TF antibody heavy chain is Gly56. These two amino acids form a primary sequence Asn-Gly that is easily deamidated. Therefore, the possibility of suppressing deamidation of Asn55 by substituting this Gly56 with another amino acid was considered. Thus, the present inventors prepared mutants in which the glycine adjacent to the asparagine was substituted with other amino acids, and their binding activities were measured. As a result, it was discovered that substitution of the glycine located adjacent to asparagine with other amino acids did not reduce the activity of the antibody, and also suppressed the known instability due to deamidation.

Thus, the present inventors found that antibody activity is not influenced by the substitution of a glycine located adjacent to asparagine with other amino acids, instead of the substitution of the asparagine itself, and thereby completed the present invention.

Specifically, the present invention provides the following:

(1) a method for stabilizing a protein, which comprises the step of substituting an amino acid that is located adjacent to an amino acid being deamidated with another amino acid;

(2) the method for stabilizing a protein of (1), wherein the amino acid being deamidated is asparagine;

(3) the method for stabilizing a protein of (1), wherein the amino acid that is located adjacent to the C-terminal side of the amino acid being deamidated is glycine;

(4) the method for stabilizing a protein of any one of (1) to (3), wherein the protein is an antibody;

(5) the method for stabilizing a protein of (4), wherein the antibody is humanized antibody;

(6) the method for stabilizing a protein of (4) or (5), wherein the amino acid being deamidated exists in the complementarity determining region (CDR);

(7) the method for stabilizing a protein of (6), wherein the complementarity determining region (CDR) is CDR2;

(8) the method for stabilizing a protein of any one of (1) to (3), wherein the protein is an antigen binding protein;

(9) the method for stabilizing a protein of any one of (1) to (3), wherein the protein belongs to the immunoglobulin superfamily;

(10) the method for stabilizing a protein of any one of (1) to (3), wherein the protein is a pharmaceutical agent;

(11) a protein stabilized by the method of any one of (1) to (10); and

(12) the stabilized protein of (11) whose antigen binding activity is 70% or more of the activity before the amino acid substitution.

The terms described in the specification are defined as follows. However, it should be understood that the definitions are provided to facilitate understanding of the terms used herein and are not to be construed as limiting the present invention.

The term "protein" herein refers to recombinant proteins, natural proteins and synthetic peptides prepared by artificially combining amino acids, which proteins and peptides consist of five amino acids or more. Proteins consist of amino acid sequences having preferably 14 residues or more, more preferably 30 residues or more, and much more preferably 50 residues or more.

The term "antibody," as used in the stabilization method of the present invention, is used in the broadest sense and includes monoclonal antibodies (including full-length monoclonal antibodies), polyclonal antibodies, mutant antibodies, antibody fragments (for example, Fab, $F(ab')_2$ and Fv) and multispecific antibodies (for example, bispecific antibodies) as long as they have the desired biological activity. Antibodies (Ab) and immunoglobulins (Ig) are glycoproteins that share the same structural features. Antibodies show a specific binding ability to a certain antigen, while immunoglobulins include antibodies and other antibody-like molecules that lack antigen specificity. Natural antibodies and immunoglobulins are generally heterotetramers of about 150,000 Daltons consisting of 2 identical light chains (L chains) and 2 identical heavy chains (H chains). Each of the light chains is connected to a heavy chain through a single covalent disulfide bond. However, the number of disulfide bonds between the heavy chains varies depending on the isotype of the immunoglobulin. Both the heavy and light chains further have intramolecular disulfide bridges at constant distance. Each of the heavy chains has a variable region (VH) at one end and many constant regions connected thereto. Each of the light chains has a variable region (VL) at one end and a constant region at the other end. The constant region and the variable region of the light chain are placed side-by-side to the first constant region and the variable region of the heavy chain, respectively. Specific amino acid residues are considered to form the interface of the variable regions of the light and heavy chains (Chothia C. et al., J. Mol. Biol. 186:651-663, 1985; Novotny J., Haber E., Proc. Natl. Acad. Sci. USA 82:4592-4596, 1985).

The light chains of antibodies (immunoglobulins) derived from vertebrate species can be divided into two clearly distinct types called kappa (κ) and lambda (λ), based on the amino acid sequence of the constant region. In addition, an "immunoglobulin" can be classified into different classes based on the amino acid sequence of the constant region of the heavy chain. At least five major classes exist for immunoglobulins: IgA, IgD, IgE, IgG and IgM. The heavy chain constant regions of the different classes are called α, δ, ϵ, γ and μ, respectively. The subunit structures and three-dimensional structures of immunoglobulins of each class are well known. Furthermore, some can be further classified into subclasses (isotypes), for example, IgG-1, IgG-2, IgG-3 and IgG-4, and IgA-1 and IgA-2.

Herein, the phrase "monoclonal antibody" refers to an antibody obtained from a group of substantially homogeneous antibodies, i.e., an antibody group wherein the antibodies constituting the group are homogeneous except for naturally occurring mutants that exist in a small number. A monoclonal antibody is highly specific and interacts with a single antigenic site. Furthermore, each monoclonal antibody targets a single antigenic determinant (epitope) on an antigen, as compared to common (polyclonal) antibody preparations that typically contain various antibodies against diverse antigenic determinants. In addition to their specificity, monoclonal antibodies are advantageous in that they are produced from hybridoma cultures not contaminated with other immunoglobulins.

The qualifier "monoclonal" indicates the characteristics of antibodies obtained from a substantially homogeneous group of antibodies, and does not require that the antibodies be produced by a particular method. The monoclonal antibody used in the present invention can be produced by, for example, the hybridoma method (Kohler G. and Milstein C., Nature 256:495-497, 1975) or the recombination method (U.S. Pat. No. 4,816,567). The monoclonal antibodies used in the present invention can be also isolated from a phage antibody library (Clackson T. et al., Nature 352:624-628, 1991; Marks J. D. et al., J. Mol. Biol. 222:581-597, 1991). The monoclonal antibodies in the present specification particularly include "chimeric" antibodies (immunoglobulins), wherein (i) a part of the heavy chain and/or light chain is derived from a specific species or a specific antibody class or subclass, and (ii) the remaining portion of the chain is derived from another species or another antibody class or subclass. Furthermore, as long as they have the desired biological activity, antibody fragments thereof are also included in the present invention (U.S. Pat. No. 4,816,567; Morrison S. L. et al., Proc. Natl. Acad. Sci. USA 81:6851-6855, 1984).

The phrase "mutant antibody" refers to amino acid sequence variants of antibodies, wherein one or more amino acid residues are altered. The "mutant antibody" herein includes variously altered amino acid variants as long as they have the same binding specificity as the original antibody. Such mutants have less than 100% homology or similarity to the amino acid sequence of the original antibody, and have at least 75%, more preferably at least 80%, even more preferably at least 85%, still more preferably at least 90%, and most preferably at least 95% amino acid sequence homology or similarity to the amino acid sequence of the variable region of the heavy chain or light chain of the original antibody. The method of the present invention is equally applicable to both polypeptides, antibodies and antibody fragments; therefore, these terms are often used interchangeably.

The phrase "antibody fragment" refers to a part of a full-length antibody and generally indicates an antigen-binding region or a variable region. For example, antibody fragments include Fab, Fab', $F(ab')_2$ and Fv fragments. Papain digestion of an antibody produces two identical antigen-binding fragments called Fab fragments, each having an antigen-binding region, and a remaining fragment called "Fc" since it crystallizes easily. On the other hand, digestion with pepsin produces a $F(ab')_2$ fragment (which has two antigen-binding sites and can cross bind antigens) and another fragment (called pFc'). Other fragments include diabody (diabodies), linear antibodies, single-chain antibodies, and multispecific antibodies formed from antibody fragments. In this specification, "functional fragment" of an antibody indicates Fv, F(ab) and $F(ab')_2$ fragments.

Herein, an "Fv" fragment is the smallest antibody fragment and contains a complete antigen recognition site and a binding site. This region is a $V_H$-$V_L$ dimer, wherein the variable regions of each of the heavy chain and light chain are strongly connected by a noncovalent bond. The three CDRs of each of the variable regions interact with each other to form an antigen-binding site on the surface of the $V_H$-$V_L$ dimer. Six CDRs confer the antigen-binding site of an antibody. However, a variable region (or a half of Fv, which contains only three CDRs specific to an antigen) alone has also the ability to recognize and bind an antigen, although its affinity is lower than the affinity of the entire binding site.

Moreover, a Fab fragment (also referred to as F(ab)) further includes the constant region of the light chain and a constant region ($C_H1$) of the heavy chain. An Fab' fragment differs from the Fab fragment in that it additionally has several residues derived from the carboxyl end of the heavy chain $C_H1$ region that contains one or more cysteines from the hinge domain of the antibody. Fab'-SH indicates an Fab' wherein one or more cysteine residues of the constant region has a free thiol-group. The F(ab') fragment is produced by the cleavage of disulfide bonds between the cystines in the hinge region of the $F(ab')_2$ pepsin digest. Other chemically bound antibody fragments are also known by those skilled in the art.

The term "diabody (diabodies)" refers to a small antibody fragment having two antigen-binding sites, and the fragment contains $V_H$-$V_L$ wherein the heavy chain variable region ($V_H$) is connected to the light chain variable region ($V_L$) in the same polypeptide chain. When a short linker is used between the two regions so that the two regions cannot be connected together in the same chain, these two regions form pairs with the variable regions in another chain to create two antigen-binding sites. The diabody is described in detail in, for example, European patent No. 404,097, WO 93/11161 and Holliger P. et al. (Proc. Natl. Acad. Sci. USA 90:6444-6448, 1993).

A single-chain antibody (hereafter also referred to as a single-chain Fv or sFv) or sFv antibody fragment contains the $V_H$ and $V_L$ regions of an antibody, and these regions exist on a single polypeptide chain. Generally, an Fv polypeptide further contains a polypeptide linker between the $V_H$ and $V_L$ regions, and therefore an sFv can form a structure necessary for antigen binding. See, Pluckthun "The Pharmacology of Monoclonal Antibodies" Vol. 113 (Rosenburg and Moore eds. (Springer Verlag, New York) pp. 269-315, 1994) for a review of sFv.

A multispecific antibody is an antibody that has specificity to at least two different kinds of antigens. Although such a molecule usually binds to two antigens (i.e., a bispecific antibody), the "multispecific antibody" herein encompasses antibodies that have specificity to more than two antigens (for example, three antigens). The multispecific antibody can be a full-length antibody or fragment thereof (for example, $F(ab')_2$ bispecific antibody).

The phrase "humanized antibody" in the present invention is an antibody produced by genetic engineering. Specifically, it refers to an antibody characterized by a structure wherein a part of or the entire CDR of the hypervariable region is derived from that of a monoclonal antibody of a non-human mammal (mouse, rat, hamster, etc.), and the framework region of the variable region and constant region are those derived from human immunoglobulin. Herein, the CDR of a hypervariable region refers to the three regions (CDR1, CDR2 and CDR3) that bind directly to an antigen in a complementary manner and that exist in the hypervariable region of the variable region of an antibody. The framework region of a variable region refers to the relatively conserved four regions (framework regions; FR1, FR2, FR3 and FR4) which intervene between the three above-mentioned CDR regions. Specifically, the "humanized antibody" in the present invention refers to antibodies wherein all regions, except a part or the entire CDR of the hypervariable region of a monoclonal antibody derived from a non-human mammal, is replaced with a corresponding region of a human immunoglobulin.

Furthermore, a humanized antibody may contain residues that do not exist in either the recipient antibody or the introduced CDR or the framework sequence. Such alterations are performed to precisely optimize the capability of the antibody. Generally, all humanized antibodies essentially contain at least one, typically two variable regions. In the antibody, all or essentially all of the CDRs correspond to the CDRs of a non-human immunoglobulin, and all or essentially all of the FRs are derived from a human immunoglobulin variable region. Optimally, the humanized antibody may contain, typically, at least a part of the constant region of a human immunoglobulin. More details can be found in Jones P. T. et al. (Nature 321:522-525, 1986), Riechmann L. et al. (Nature 332:323-327, 1988) and Presta et al. (Curr. Op. Struct. Biol. 2:593-596, 1992).

The term "variable" in the antibody variable region indicates that a certain region in the variable region varies highly among antibodies, and that the region is responsible for the binding and specificity of antibodies to their respective specific antigens. The variable regions are concentrated in three areas called CDRs or hypervariable regions within the variable regions of light and heavy chains. There are at least two methods to determine the CDR: (1) a technique based on sequence variation among species (i.e., Kabat et al., "Sequence of Proteins of Immunological Interest" (National Institute of Health, Bethesda) 1987); and (2) a technique based on crystallographic research of the antigen-antibody complex (Chothia C. et al., Nature 342:877-883, 1989). The area more highly conserved in the variable region is called FR. The variable regions of natural heavy and light chains mainly have β-sheet structures and form three loop-like connections, and in some cases, contain four FRs connected by CDRs that form a β-sheet structure. The CDRs in each chain are maintained very closely to the CDRs on the other chain by FRs and play a role in the formation of the antigen-binding site of an antibody (see, Kabat et al.). The constant region does not directly participate in the binding of the antibody to the antigen. However, it displays various effector functions, such as participation of the antibody in antibody dependent cytotoxicity.

The constant region of a human immunoglobulin has a unique amino acid sequence for each isotype, such as IgG (IgG1, IgG2, IgG3 and IgG4), IgM, IgA, IgD and IgE. In the present invention, the constant region of the above-mentioned humanized antibody may be of any isotype. Preferably, the constant region of human IgG is used. Moreover, there is no limitation on the FR of the variable region derived from a human immunoglobulin.

The term "antigen" in the present specification encompasses both complete antigens having immunogenicity and incomplete antigens (including haptens) without immunogenicity. Antigens include substances such as proteins, polypeptides, polysaccharides, nucleic acids and lipids; however, they are not limited thereto. As immunogens for antibody production, soluble antigens or fragments thereof connected to other molecules may be used. For transmembrane molecules, such as receptors, fragments thereof (for example, extracellular regions of receptors) may be used as immunogens. Alternatively, cells expressing transmembrane molecules may be used as immunogens. Such cells may be natural cells (for example, tumor cell lines) or cells transfected by recombinant techniques to express the transmembrane molecules. Any form of an antigen known to those skilled in the art can be used to produce antibodies.

Herein, the phrase "antigen-binding protein" refers to proteins that have the ability to bind to an antigen.

The phrase "immunoglobulin superfamily" in the present specification refers to proteins that have the structural characteristic wherein one or multiple domains homologous to the constant or variable domain of an immunoglobulin are contained. The immunoglobulin superfamily includes the immunoglobulin (H chain and L chain), T cell receptor (αchain, βchain, γ chain and δ chain), MHC class 1 molecule (α chain), $β_2$ microglobulin, MHC class II molecule (α chain and β chain), CD3 (γ chain, δ chain and ε chain), CD4, CD8 (α chain and β chain), CD2, CD28, LFA-3, ICAM-1, ICAM-2, VCAM-1, PECAM-1, $F_C$ receptor II, poly Ig receptor, Thy-1, NCAM, myelin-associated glycoprotein (MAG), Po, carcinoembryonic antigen (CEA), PDGF receptor and so on.

The phrase "pharmaceutical agent" in the present specification refers to substances that are administered to animals for purposes such as treatment or prevention of diseases, injuries and such, or improvement of health conditions.

1. Amino Acid Alteration for Protein Stabilization

The present invention provides a method for stabilizing a protein wherein an amino acid adjacent to an amino acid subject to deamidation in the protein is substituted with another amino acid. The protein to be stabilized according to the present invention is not restricted in any way. A suitable example of the protein includes antibodies. Humanized antibodies or human antibodies are preferred as the antibody for medical use.

In addition to asparagine, glutamine is also known as an amino acid that is deamidated (Scotchler J. W. and Robinson A. B., Anal. Biochem. 59:319-322, 1974). When comparing peptides of 5 amino acids, the half-life of glutamine is 96 to 3409 days compared to the half-life of asparagine being 6 to 507 days. That is, the reaction rate of deamidation of glutamine is very slow compared with that of asparagine (Bischoff R. and Kolbe H. V. J., J. Chromatogr. B. 662:261-278, 1994). Deamidation of glutamine has not been detected in antibody preparations (Harris R. J., Kabakoff B., Macchi F. D., Shen F. J., Kwong M., Andya J. D. et al., J. Chromatogr. B. 752:233-245, 2001). However, the deamidation reaction is supposed to be enhanced in vivo compared to in pharmaceutical preparations (Robinson N. E. and Robinson A. B., Proc. Natl. Acad. Sci. USA 98:12409-12413, 2001). Therefore, to develop an antibody preparation with a long in vivo half-life, suppression of deamidation of glutamine as well as asparagine is considered to be necessary. The amino acid to be deamidated preferably is asparagine.

Amino acids other than glycine can be also considered as the amino acid adjacent to a deamidated amino acid and that can be substituted in a protein (Robinson N. E. and Robinson A. B., Proc. Natl. Acad. Sci. USA 98:4367-4372, 2001). However, glycine is particularly known to cause deamidation of asparagine. Thus, the amino acid that is located adjacent to an amino acid that is deamidated preferably is glycine.

Generally, an antibody is inactivated by amino acid substitution in the CDR. However, the present inventors found that the activity of an antibody is retained even after the substitution of an amino acid adjacent to asparagine in the CDR, and hence the stability of the antibody can be improved. Therefore, according to the present invention, an amino acid adjacent to an asparagine in the CDR is effectively substituted with another amino acid. Glycine is a suitable target as the amino acid adjacent to the asparagine. Particularly, glycine contained in the "Asn-Gly" sequence that is particularly easily deamidated is the most suitable target.

According to the present invention, in addition to the amino acid adjacent to the above-mentioned deamidated amino acid, one or more other amino acids can also be altered, unless the stability and biological activity of the protein is thereby reduced. When the protein is an antibody, biological activity denotes its ability to specifically bind to an antigen. A preferred amino acid alteration is a conservative substitution from the viewpoint of maintaining the property of the protein.

The alteration of an amino acid of a protein can be performed by methods that recombine the gene sequence encoding the protein. Techniques generally known in the art can be used for gene recombination.

When the protein is an antibody, the alteration of amino acids can be performed as follows. For example, variant antibodies or mutants wherein one or more amino acid residues are altered in one or more of the hypervariable regions of the antibody can be prepared. In addition, one or more mutations (for example, substitution) can be introduced into the framework residues of the mammalian antibody to improve the binding affinity of the mutant antibody for its antigen. Exemplary framework residues that can be altered include portions that directly bind to antigens by noncovalent bonds (Amit A. G. et al., Science 233:747-753, 1986), portions that affect and/or influence the structure of the CDR (Chothia C. and Lesk A. M., J. Mol. Biol. 196:901-917, 1987) and/or portions that are involved in the VL-VH interaction (European patent No. 239,400, B1). According to one embodiment, the binding affinity of an antibody to an antigen is enhanced by altering one or more of such framework residues.

One useful method for producing mutant antibodies is "Alanine-Scanning Mutagenesis" (Cunningham B. C. and Wells J. A., Science 244:1081-1085, 1989; Cunningham B. C. and Wells J. A., Proc. Natl. Acad. Sci. USA 84:6434-6437, 1991). According to this method, one or more residues of the hypervariable region are substituted with alanine or polyalanine residues to change the interaction between the antigen and the corresponding amino acids. The residues of the hypervariable region that showed functional sensitivity to the substitution are further distinguished in more detail by introducing further or different mutations to the substitution site. Therefore, although the site for introducing an amino acid sequence mutation is determined beforehand, the type of mutation does not have to be determined beforehand.

The Ala mutant produced by this method is screened for its biological activity. Depending on the desired characteristics obtained by the scanned residues, similar substitution of other amino acids may also be performed. Alternatively, there is also a method wherein the altered amino acid residue is more systematically identified. According to this method, the hypervariable region residues within a species-specific antibody involved in the binding of a first mammalian species antigen and the hypervariable region residues involved in the binding of a homologous antigen of a second mammalian species can be identified. In order to achieve this, Alanine-scanning is performed for the hypervariable region residues of the species-specific antibody. In the scanning, the binding of each Ala mutant to the first and second mammalian species antigens is tested in order to identify (1) the hypervariable region residues involved in the binding of the first mammalian species (for example, human) antigen and (2) the site involved in the binding of the second mammalian species (for example, non-human) antigen homolog. Preferably, residues that are apparently involved in the binding of the second mammalian species (for example, non-human mammalian) derived-antigen, but not in the binding of the first mammalian species (for example, human) derived-antigens are candidates for alteration. In another embodiment, residues that are clearly involved in the binding of the first and second mammalian species derived-antigens are selected for alteration. An alteration can include (i) deletion of the residues or (ii) insertions wherein one or more residues are linked to the target residues; however, generally, alteration refers to substitution of the residues with other amino acids.

A nucleic acid molecule encoding an amino acid sequence mutant may be prepared by various methods known in the art.

Such methods include, but are not limited to, oligonucleotide mediated mutation (or site-specific mutation), PCR mutation or cassette mutation of a previously produced mutated or a non-mutated version of a species-specific antibody. Suitable methods for producing mutants include site-specific mutation (see Kunkel T. A., Proc. Natl. Acad. Sci. USA 82:488-492, 1985) and such. Generally, mutant antibodies having improved biological characteristics have at least 75%, preferably at least 80%, more preferably at least 85%, further more preferably at least 90% and most preferably at least 95% amino acid sequence homology or similarity with the amino acid sequence of the variable region of the heavy or light chain of the original antibody. Sequence homology or similarity in the present specification is defined as the rate of the amino acid residues which are homologous (i.e., the same residues) or similar (i.e., the amino acid residues of the same group based on the above-mentioned general side chain characteristic) to the residues in the species-specific antibody of the candidate sequence after alignment of the sequence and introducing a gap as needed in order to obtain the maximum sequence homology.

Alternatively, a mutant antibody can be constructed by systematic mutations of the CDR in the heavy and light chains of an antibody. Preferable methods for constructing such a mutant antibody include methods utilizing affinity maturation using phage display (Hawkins R. E. et al., J. Mol. Biol. 226:889-896, 1992; Lowman H. B. et al., Biochemistry 30:10832-10838, 1991). Bacteriophage coat protein fusion (Smith G. P., Science 228:1315-1317, 1985; Scott J. K. and Smith G. P., Science 249:386-390, 1990; Cwirla S. E. et al., Proc. Natl. Acad. Sci. USA 87:6378-6382, 1990; Devlin J. J. et al., Science 249:404-406, 1990; review by Wells and Lowman, Curr. Opin. Struct. Biol. 2:597, 1992; U.S. Pat. No. 5,223,409) is known as a useful method to relate a displayed phenotype protein or peptide to the genotype of the bacteriophage particle encoding it. Moreover, a method to display the F(ab) region of an antibody on the surface of a phage is also known in the art (McCafferty et al., Nature 348:552, 1990; Barbas et al., Proc. Natl. Acad. Sci. USA 88:7978, 1991; Garrard et al., Biotechnology 9:1373, 1991). Monovalent phage display comprises the step of displaying a group of protein variants as fusions with a coat protein of the bacteriophage, yet only one copy of the variant is displayed on a few phage particles (Bass et al., Proteins 8:309, 1990).

Affinity maturation or improvement of equilibrium of the binding affinity of various proteins has been performed hitherto by mutagenesis, monovalent phage display, functional analysis and addition of desirable mutations of, for example, human growth hormone (Lowman and Wells, J. Mol. Biol. 234:564-578, 1993; U.S. Pat. No. 5,534,617) and antibody F(ab) region (Barbas et al., Proc. Natl. Acad. Sci. USA 91:3809, 1994; Yang et al., J. Mol. Biol. 254:392, 1995). A library of many protein variants ($10^6$ molecules) differing at specific sequence sites can be prepared on the surface of bacteriophage particles that contain DNAs encoding specific protein variants. The displayed amino acid sequence can be predicted from DNA by several cycles of affinity purification using immobilized antigen, followed by isolation of respective bacteriophage clones.

2. Production of Polyclonal Antibodies

Polyclonal antibodies are preferably produced in non-human mammals by multiple subcutaneous (sc) or intraperitoneal (ip) injections of related antigen and adjuvant. The related antigen may be bound to a protein that is immunogenic to the immunized species, for example, keyhole limpet hemocyanin, serum albumin, bovine thyroglobulin or soybean trypsin inhibitor, using bifunctional agents or inducers, for example, maleimidebenzoylsulfosuccinimide ester (binding via a cysteine residue), N-hydroxysuccinimide (via a lysine residue), glutaraldehyde, succinic anhydride, thionylchloride or $R^1N{=}C{=}CR$ (wherein, R and $R^1$ are different alkyl groups).

For example, an animal is immunized against an antigen, an immunogenic conjugate or a derivative through multiple endermic injections of solution containing 100 μg or 5 μg of protein or conjugate (amounts for rabbit or mouse, respectively) with 3 volumes of Freund's complete adjuvant. One month later, a booster is applied to the animal through subcutaneous injections of ⅕ to ⅒ volume of the original peptide or conjugate in Freund's complete adjuvant at several sites. Blood is collected from the animal after 7 to 14 days and serum is analyzed for antibody titer. Preferably, a conjugate of the same antigen bound to a different protein and/or bound via a different cross-linking reagent is used as the booster. A conjugate can be also produced by protein fusion through recombinant cell culture. Moreover, in order to enhance immune response, agglutinins, such as alum, are preferably used. The selected mammalian antibody usually has a strong enough binding affinity for the antigen. The affinity of an antibody can be determined by saturation bonding, enzyme-linked immunosorbent assay (ELISA) and competitive analysis (for example, radioimmunoassay).

As a method of screening for desirable polyclonal antibodies, conventional cross-linking analysis described in "Antibodies, A Laboratory Manual" (Harlow and David Lane eds., Cold Spring Harbor Laboratory, 1988) can be performed. Alternatively, for example, epitope mapping (Champe et al., J. Biol. Chem. 270:1388-1394, 1995) may be performed. Preferred methods for measuring the efficacy of a polypeptide or antibody include a method using quantitation of the antibody binding affinity. Other embodiments include methods wherein one or more of the biological properties of an antibody other than the antibody binding affinity are evaluated. These analytical methods are particularly useful in that they indicate the therapeutic efficacy of an antibody. Antibodies that show improved properties through such analysis generally, but not always, also have enhanced binding affinity.

3. Production of Monoclonal Antibodies

A monoclonal antibody is an antibody that recognizes a single antigen site. Due to its uniform specificity, a monoclonal antibody is generally more useful than a polyclonal antibody that contains antibodies recognizing many different antigen sites. A monoclonal antibody can be produced by the hybridoma method (Kohler et al., Nature 256:495, 1975), the recombinant DNA method (U.S. Pat. No. 4,816,567), and so on.

According to the hybridoma method, a suitable host animal, such as mouse, hamster or rhesus monkey, is immunized in a manner similar to that described above to produce antibodies that specifically bind to a protein used for immunization or to induce lymphocytes to produce the antibodies. Alternatively, a lymphocyte may be immunized in vitro. Then, the lymphocyte is fused with a myeloma cell using suitable fusion agents, such as polyethylene glycol, to generate a hybridoma cell (Goding, "Monoclonal Antibodies: Principals and Practice", Academic Press, pp. 59-103, 1986). Preferably, the produced hybridoma cell is seeded and cultured on a proper culture media containing one or more substances that inhibit proliferation or growth of unfused parental myeloma cells. For example, when the parental myeloma cell lacks the hypoxanthine guanine phosphoribosyl transferase enzyme (HGPRT or HPRT), the culture medium for the hybridoma typically contains substances that inhibit the growth of HGRPT deficient cells, i.e., hypoxantin, aminopterin and thymidine (HAT culture media).

Preferred myeloma cells include those that can efficiently fuse, can produce antibodies at a stable high level in selected antibody producing cells, and are sensitive to media such as HAT media. Among the myeloma cell lines, preferred myeloma cell lines include mouse myeloma cell lines, such as mouse tumor derived cells MOPC-21 and MPC-11 (obtained from Salk Institute Cell Distribution Center, San Diego, USA), and SP-2 and X63-Ag8-653 cells (obtained from the American Type Culture Collection, Rockville, USA). Human myeloma and mouse-human heteromyeloma cell lines have also been used for the production of human monoclonal antibodies (Kozbar, J. Immunol. 133:3001, 1984; Brodeur et al., "Monoclonal Antibody Production Techniques and Application", Marcel Dekker Inc, New York, pp. 51-63, 1987).

Next, the production of monoclonal antibodies against an antigen in the culture media wherein the hybridoma cells had been cultured is analyzed. Preferably, the binding specificity of the monoclonal antibody produced from the hybridoma cells is measured by in vitro binding assay, such as immunoprecipitation, radioimmunoassay (RIA) or enzyme-linked immunosorbent assay (ELISA). After identifying the hybridoma cells that produce antibodies having the desired specificity, affinity and/or activity, clones are subcloned by a limiting dilution method and cultured by standard protocols (Goding, "Monoclonal Antibodies: Principles and Practice", Academic Press, pp. 59-103, 1986). Culture media suitable for this purpose include, for example, D-MEM and RPMI-1640. Furthermore, a hybridoma cell can also be grown as ascites tumor in an animal in vivo. Monoclonal antibodies secreted from a subclone are preferably purified from culture media, ascites or serum via conventional immunoglobulin purification methods, such as protein A-Sepharose, hydroxyapatite chromatography, gel electrophoresis, dialysis or affinity chromatography.

DNA encoding a monoclonal antibody can be easily isolated and sequenced by conventional methods, for example, using an oligonucleotide probe specifically binding to genes encoding the heavy and light chains of the monoclonal antibody. Hybridoma cells are preferred starting materials for obtaining such DNAs. Once the DNA is isolated, it is inserted into an expression vector and transformed into a host cell, such as an *E. coli* cell, simian COS cell, Chinese hamster ovary (CHO) cell or myeloma cell, that produces no immunoglobulin protein unless transformed, and the monoclonal antibody is produced from the recombinant host cell. In another embodiment, an antibody or an antibody fragment can be isolated from an antibody phage library prepared by the method described by McCafferty et al. (Nature 348: 552-554, 1990). Clackson et al. (Nature 352: 624-628, 1991) and Marks et al. (J. Mol. Biol. 222: 581-597, 1991) describe the isolation of mouse and human antibodies using phage libraries, respectively. The following references describe the production of high affinity (nM range) human antibody by chain shuffling (Marks et al., Bio/Technology 10:779-783, 1992), and combinatorial infection and in vivo recombination for producing large phage libraries (Waterhouse et al., Nucl. Acids Res. 21:2265-2266, 1993). These techniques can also be used to isolate monoclonal antibodies in place of conventional monoclonal antibody hybridoma techniques.

DNA can be also altered by, for example, substitution of corresponding mouse sequences with the coding sequences of the constant regions of human heavy and light chains (U.S. Pat. No. 4,816,567; Morrison et al., Proc. Natl. Acad. Sci. USA 81:6851, 1984), or by binding immunoglobulin polypeptides through covalent bonds. Typically, these non-immunoglobulin polypeptides are substituted with the constant region of an antibody, or the variable region of the antibody's antigen-binding site is substituted to construct a chimeric bispecific antibody that has an antigen-binding site specific for an antigen and another antigen-binding site specific for another antigen.

4. Production of Antibody Fragments

Hitherto, antibody fragments have been produced by digesting a natural antibody with proteases (Morimoto et al., J. Biochem. Biophys. Methods 24:107-117, 1992; Brennan et al., Science 229:81, 1985). However, today they can also be produced by recombinant techniques. For example, antibody fragments can also be isolated from the above-mentioned antibody phage library. Furthermore, $F(ab')_2$-SH fragments can be directly collected from a host cell such as *E. coli*, and chemically bound in the form of $F(ab')_2$ fragments (Carter et al., Bio/Technology 10:163-167, 1992). Moreover, in another method, $F(ab')_2$ fragments can also be directly isolated from recombinant host cell culture. The method for constructing single chain antibodies, fragments of single chain antibodies and such are well known in the art (for example, see, U.S. Pat. Nos 4,946,778; 5,260,203; 5,091,513; 5,455,030; etc.).

5. Production of Multispecific Antibodies

Methods for producing multispecific antibodies are known in the art. The production of a full-length bispecific antibody includes the step of co-expression of two immunoglobulin heavy-light chains having different specificity (Millstein et al., Nature 305:537-539, 1983). The heavy and light chains of immunoglobulins are randomly combined, and therefore, the obtained multiple co-expressing hybridomas (quadroma) are a mixture of hybridomas, each expressing a different antibody molecule. Thus, the hybridoma producing the correct bispecificity antibody has to be selected from among them. The selection can be performed by methods such as affinity chromatography. Furthermore, according to another method, the variable region of an antibody having the desired binding specificity is fused to the constant region sequence of an immunoglobulin. The above-mentioned constant region sequence preferably contains at least a part of the hinge, CH2 and the CH3 regions of the heavy chain constant region of the immunoglobulin. Preferably, the CH1 region of the heavy chain required for the binding with the light chain is further included. DNA encoding the immunoglobulin heavy chain fusion is inserted into an expression vector to transform a proper host organism. If needed, DNA encoding the immunoglobulin light chain is also inserted into an expression vector different from that of the immunoglobulin heavy chain fusion, to transform the host organism. There are cases where the antibody yield increases when the ratio of the chains is not identical. In such cases, it is more convenient to insert each of the genes into separate vectors since the expression ratio of each of the chains can be controlled. However, genes encoding plural chains can also be inserted into a vector.

According to a preferred embodiment, a bispecific antibody is desired wherein (i) a heavy chain having a first binding specificity exists as an arm of the hybrid immunoglobulin and (ii) a heavy chain-light chain complex having another binding specificity exists as the other arm. Due to the existence of the light chain on only one of the arms, the bispecific antibody can be readily isolated from other immunoglobulins. Such a separation method is referred to in WO 94/04690. See, Suresh et al. (Methods in Enzymology 121:210, 1986) for further reference to methods for producing bispecific antibodies. A method wherein a pocket corresponding to a bulky side chain of a first antibody molecule is created in a multispecific antibody that comprises the antibody constant region CH3 (WO 96/27011) is also known as a method for decreasing homodimers to increase the ratio of heterodimers in the final product obtained from recombinant cell culture. According to the method, one of the antibody molecules is altered by replacing (a) one or more amino acids on the surface that binds to the other molecule, with (b) amino acids having a bulky side chain (e.g., tyrosine or tryptophan). Furthermore, amino acids with a bulky side chain in the corresponding portion of the other antibody molecule can be replaced with amino acids with a small side chain (e.g., alanine or threonine).

Bispecific antibodies include, for example, heteroconjugated antibodies wherein one antibody is bound to avidin and the other to biotin and such (U.S. Pat. No. 4,676,980, WO 91/00360, WO 92/00373, European patent No. 03089). Cross-linkers used for the production of such heteroconjugated antibodies are well known, and are mentioned, for example, in U.S. Pat. No. 4,676,980.

Additionally, methods for producing bispecific antibodies from antibody fragments also have been reported. For example, bispecific antibodies can be produced utilizing chemical bonds. For example, first, $F(ab')_2$ fragments are produced and the fragments are reduced in the presence of a dithiol complexing agent, sodium arsanilate, to prevent intramolecular disulfide formation. Next, the $F(ab')_2$ fragments are converted to thionitrobenzoate (TNB) derivatives. After re-reducing one of the $F(ab')_2$-TNB derivatives to a Fab'-thiol using mercaptoethanolamine, equivalent amounts of the $F(ab')_2$-TNB derivative and Fab'-thiol are mixed to produce a bispecific antibody.

Various methods have been reported to directly produce and isolate bispecific antibodies from recombinant cell culture. For example, a production method for bispecific antibodies using a leucine zipper has been reported (Kostelny et al., J. Immunol. 148:1547-1553, 1992). First, leucine zipper peptides of Fos and Jun proteins are connected to the Fab' sites of different antibodies by gene fusion, the homodimer antibodies are reduced at the hinge region to form monomers, followed by reoxidation to form a heterodimer antibody. Alternatively, a method to form two antigen-binding sites has been reported wherein pairs are formed between different complementary light chain variable regions (VL) and heavy chain variable regions (VH) by linking the VL and VH through a linker that is short enough to prevent binding between these two regions (Hollinger et al., Proc. Natl. Acad. Sci. USA 90:6444-6448, 1993). Furthermore, dimers utilizing single chain Fv (sFV) have also been reported (Gruger et al., J. Immunol. 152:5368, 1994). Moreover, trispecific (rather than bispecific) antibodies have also been reported (Tutt et al., J. Immunol. 147:60, 1991).

6. Production of Humanized Antibodies

Humanized antibodies can be obtained via established general antibody production methods by using an immunogen (antigen) to immunize a transgenic non-human mammal capable of producing human antibodies. Methods for producing human antibody producing-non-human mammals, particularly human antibody-producing transgenic mice, are known in the art (Nature Genetics 7:13-21, 1994; Nature Genetics 15:146-156, 1997; Published Japanese Translation of International Publication No. Hei 4-504365; Published Japanese Translation of International Publication No. Hei 7-509137; Nikkei Science 6:40-50, 1995; WO 94/25585; Nature 368:856-859, 1994; Published Japanese Translation of International Publication No. Hei 6-500233; etc.). Specifically, the human antibody-producing transgenic non-human mammal can be produced by the following steps:

(1) producing a knockout non-human mammal wherein the endogenous immunoglobulin heavy chain gene of the animal is functionally inactivated via the substitution of at least a part of the endogenous immunoglobulin heavy chain locus of the non-human mammal with a drug resistance marker gene (for example, neomycin resistance gene) by homologous recombination;

(2) producing a knockout non-human mammal wherein the endogenous immunoglobulin light chain gene (particularly, the K chain gene) of the animal is functionally inactivated via the substitution of at least a part of the endogenous immunoglobulin light chain locus of the non-human mammal with a drug resistance marker gene (for example, neomycin resistance gene) by homologous recombination;

(3) producing a transgenic non-human mammal wherein a desired region of the human immunoglobulin heavy chain locus has been integrated into the mouse chromosome using a vector represented by a yeast artificial chromosome (YAC) vector or similar that can transfer large genes;

(4) producing a transgenic non-human mammal wherein a desired region of the human immunoglobulin light chain (particularly, the K chain) locus has been integrated into the mouse chromosome using a vector represented by YAC vector and such that can transfer large genes; and (5) producing a transgenic non-human mammal wherein both the endogenous immunoglobulin heavy chain and light chain loci of the non-human mammal are functionally inactivated, yet desired regions of both the human immunoglobulin heavy chain and light chain are integrated into the non-mammalian chromosome by crossing the knockout non-human mammals and transgenic non-human mammals of above-mentioned (1) to (4) in an arbitrary order.

As mentioned above, an endogenous immunoglobulin locus of non-human mammals can be inactivated so that it inhibits reconstitution of the locus via the substitution of a proper region of the locus with an exogenous marker gene (for example, neomycin resistance gene, etc.) via homologous recombination. For inactivation using the homologous recombination, for example, a method called positive negative selection (PNS) can be used (Nikkei Science 5:52-62, 1994). The functional inactivation of an immunoglobulin heavy chain locus can be attained by, for example, introducing a deficit into a part of the J or C region (for example, the Cμ region). On the other hand, the functional inactivation of an immunoglobulin light chain (for example, the κ chain) can be attained by, for example, introducing a deficit into a part of the J or C region, or a region comprising the area that spans over both the J and C regions.

A transgenic animal can be produced by standard methods (for example, "Saishin-Dobutsusaibou-Jikken manual (The latest animal cell experiment manual)", Chapter 7, LIC, pp. 361-408, 1990). Specifically, a hypoxanthine-guanine phosphoribosyltransferase (HRPT) negative embryonic stem (ES) cell derived from a normal non-human animal blastocyst is fused by the spheroplast fusion method with yeast that comprises a YAC vector inserted with a gene or a part thereof encoding the human immunoglobulin heavy chain or light chain locus and the HRPT gene. The ES cell wherein the exogenous gene has been integrated into the mouse endogenous gene is selected by HAT selection. Subsequently, the selected ES cell is microinjected into a fertilized egg (blastocyst) obtained from another normal non-human mammal (Proc. Natl. Acad. Sci. USA 77:7380-7384, 1980; U.S. Pat. No. 4,873,191). A chimeric transgenic non-human mammal is born by transplanting the blastocyst into the uterus of another non-human mammal that acts as the surrogate mother. Heterotransgenic non-human mammals are obtained by crossing the chimeric animal with a normal non-human mammal. By crossing the heteroanimals among themselves, homotransgenic non-human mammals can be obtained according to Mendel's law.

A humanized antibody can also be obtained from the culture supernatant by culturing a recombinant human monoclonal antibody-producing host that can be obtained via the transformation of the host with cDNAs encoding each of the heavy and light chains of such humanized antibody or preferably a vector containing the cDNAs by recombinant techniques. Herein, such a host is a eukaryotic cell other than a fertilized egg, preferably a mammalian cell, such as CHO cell, lymphocyte or myeloma cell.

The antigen-binding activity of an antibody stabilized by the method of the present invention is not particularly limited; however, it is preferred to have 70% or more, more preferably 80% or more and further preferably 90% or more of the activity possessed by the antibody before the amino acid substitution.

BRIEF DESCRIPTION OF THE DRAWINGS

FIG. 1 depicts the amino acid sequences of humanized heavy chain version i (SEQ ID NO:25) and humanized light chain version b2 (SEQ ID NO:26) contained in the anti-human TF antibody described in WO 99/51743. A few asparagine residues (Asn28, Asn51 and Asn55) that may be deamidated are boxed.

FIG. 2 depicts the cloning vector pCVIDEC-AHi integrated with the heavy chain variable region (AHi) of the anti-human TF antibody. A: the entire pCVIDEC-AHi vector; and B: the NheI-SalI fragment of the heavy chain variable region.

FIG. 3 depicts the anion exchange chromatogram of each of the anti-human TF mutant antibodies and the original anti-human TF antibody. A: 99D01; and B: original (native).

FIG. 4 depicts the anion exchange chromatogram of each of the anti-human TF mutant antibodies and the original anti-human TF antibody. C: N28D; and D: N51D.

FIG. 5 depicts the anion exchange chromatogram of each of the anti-human TF mutant antibodies and the original anti-human TF antibody. E: N55D; and F: N51D/N55D.

FIG. 9 depicts the cloning vector pCVIDEC-AHi integrated with the heavy chain variable region (AHi) of the anti-human TF antibody. The nucleotide sequences described in FIG. 9 are shown in SEQ ID NOs: 27 and 28. A: the entire pCVIDEC-AHi vector; B: the XbaI-BalI fragment of the heavy chain variable region; and C: the XbaI-ApoI fragment of the heavy chain variable region.

DETAILED DESCRIPTION

Figure 6:
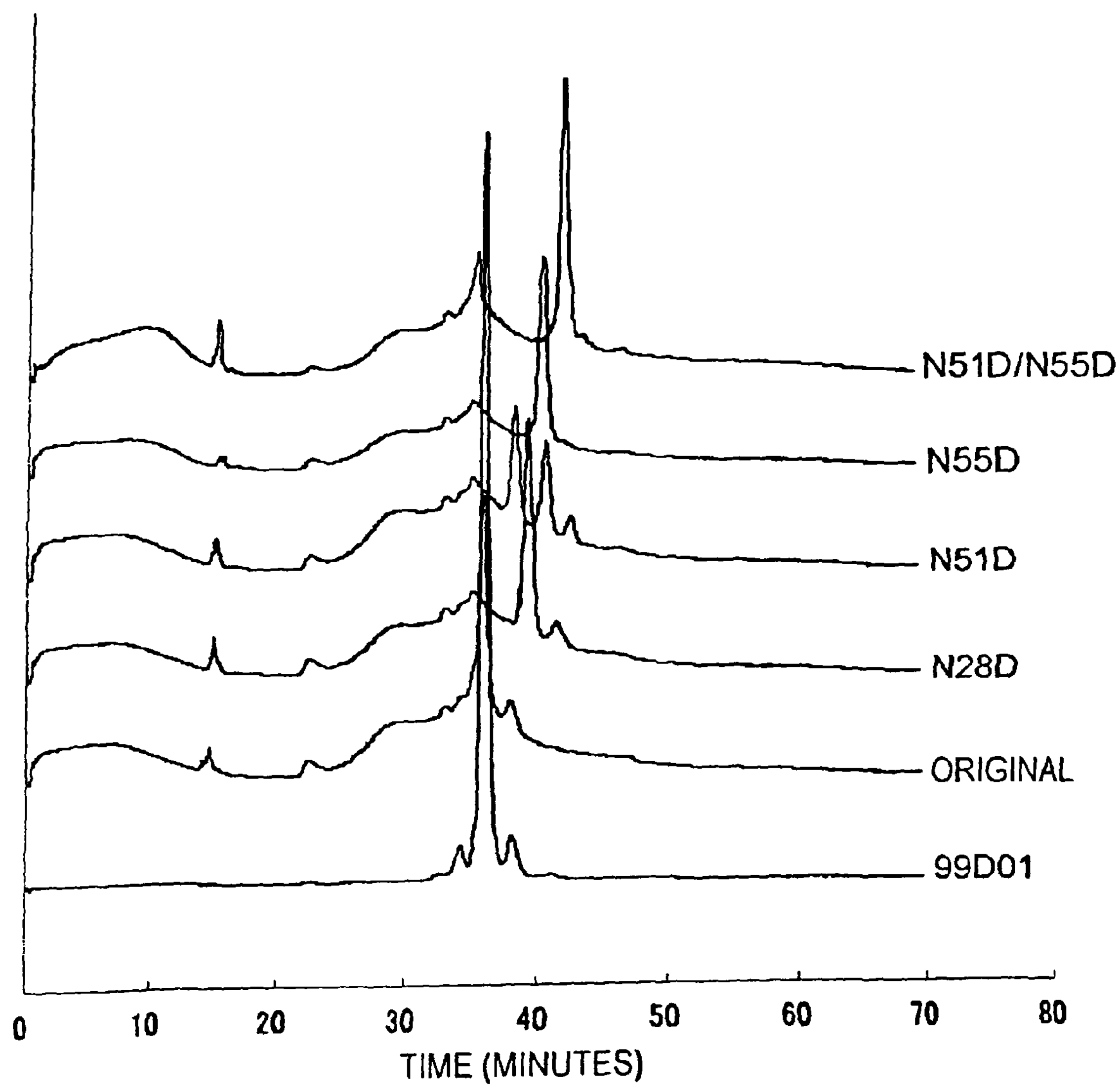
FIG. 6 depicts the superposed anion exchange chromatograms of each of the anti-human TF mutant antibodies and the original anti-human TF antibody.

Herein below, the present invention will be specifically described using Examples; however, it is not to be construed as being limited thereto:

Example 1

Measurement of Binding and Neutralizing Activities of Anti-Human TF Antibody Asn55 Substitution Mutant with TF Humanized antibody against human tissue factor (TF) described in WO 99/51743 is expected to suppress thrombus formation without suppressing the extrinsic blood coagulation reaction through the inhibition of the TF mediated Factor X activation in the intrinsic blood coagulation reaction. This anti-human TF antibody contains humanized heavy chain version i (SEQ ID NO: 25, FIG. 1) and humanized light chain version b2 (SEQ ID NO: 26, FIG. 1). The antibody comprises a few asparagine residues that may be deamidated: such as Asn51 and Asn55 in CDR2 of the heavy chain variable region, and Asn28 in FR1 of the heavy chain variable region. Particularly, Asn55 is contained in an Asn-Gly sequence, and thus is considered to be easily deamidated.

A pharmaceutical formulation of the antibody has not been established. Under destabilizing conditions of the antibody, the antibody's binding to TF decreases in a solution pH-dependent manner, and an increase of low pI molecular species has been observed. Due to the increase of degeneration upon stronger basification, the decrease in the binding activity and the increase of low pI molecular species are presumed to result from the deamidation of amino acids in the anti-human TF antibody. Furthermore, deamidation is believed to occur in the CDR region due to the co-observed decrease in antigen binding activity.

Based on these findings, mutants (4 mutants including the N51D mutant, N55D mutant, N51D/N55D double mutant and N28D mutant) were prepared wherein Asn51 and Asn55 in the CDR2 and Asn28 in the FR1 of the heavy chain variable region of anti-human TF antibody described in WO 99/51743 have been substituted with aspartic acid, and their TF-binding activity and TF-neutralizing activity were measured.

The amino acid sequence of the antibody follows the sequence described by Kabat et al. (Kabat E. A., Wu T. T., Perry H. M., Gottesman K. S. and Foeller C., "Sequences of proteins of immunological interest. 5th ed.", US Dept. Health and Human Services, Bethesda, Md., 1991).

1. Construction of Anti-human TF Mutant Antibody Expression Vector

Cloning vector pCVIDEC-AHi (FIG. 2A) and anti-human TF antibody expression vector pN5KG4P-AHi-ALb2 (both containing the heavy chain variable region (AHi) of the anti-human TF antibody) were purified from $dam^{-}/dcm^{-}$ *E. coli* SCS110.

Substitution of a codon encoding Asn with one encoding Asp was performed in pCVIDEC-AHi. Specifically, a fragment of about 30 up containing the region that encodes each Asn was digested with restriction enzymes and replaced with a fragment prepared from a synthetic olio DNA having a base substitution (FIG. 2B). To alter Asn51 and Asn55, pCVIDEC-AHi was digested with XbaI and BalI, and a fragment designed for one base pair substitution of the codon was integrated to replace either or both of Asn51 and Asn55 in the heavy chain variable region CDR2 of the anti-human TF antibody with Asp. To alter Asn28, pCVIDEC-AHi was digested with MoiI and EcoT22I, and a fragment designed for one base pair substitution of the codon was integrated to substitute Asn28 with Asp in the heavy chain variable region FR1 of the anti-human TF antibody.

The sequence was confirmed at every step while constructing the expression vector. The target sequence was confirmed on the cloning vector, and the sequence was reconfirmed after replacing the fragment obtained by digestion with NheI and SalI with the heavy chain variable region of the anti-human TF antibody expression vector digested with NheI and SalI. *E. coli* DH5α was transformed after confirming that the target sequence was obtained. Then, the four anti-human TF mutant antibody expression vectors, i.e., N51D mutant expression vector, N55D mutant expression vector, N51D/N55D double mutant expression vector and N28D mutant expression vector, were purified using the QIAGEN Maxi™ column.

2. Transient Expression of Anti-human TF Mutant Antibody in COS-7 Cells

Five vectors in total, i.e., the constructed expression vectors for each of the mutants and the original anti-human TF antibody, were transfected into COS-7 cells by the electroporation method and were transiently expressed. COS-7 cells were washed with D-PBS (−) and then resuspended in PBS to about 0.3 to $1.0\times10^{7}$ cells/ml. The cell suspension was transferred into a 0.4 cm cuvette together with 10 μg of anti-human TF mutant antibody expression vector, and electroporation was conducted at 1.5 kV and 25 μF. After standing for 10 min, the cells were suspended in 30 ml of 10% FCS-DMEM. On the next day, dead cells were discarded together with the media and 50 ml of fresh 10% FCS-DMEM was added. The cells were cultured for 3 days, and then the culture supernatant was collected.

3. Measurement of Expression Level of Anti-human TF Mutant Antibody 3-1 Measurement of Expression Level by Direct ELISA 100 μl each of the culture supernatant of the transfected COS-7 cells were seeded on a 96-well ELISA plate and immobilized over night. Similarly, 100μ each of anti-human TF antibody (Lot No.00C01) serially diluted (1 to 1000 ng/ml) with DMEM was seeded and immobilized on a 96-well ELISA plate for plotting a calibration curve. After blocking with ELISA dilution buffer, HRP-labeled anti-IgG antibody was reacted and color was developed by TMB. The reaction was quenched with 2 M sulfuric acid and the absorbance at 450 nm was measured with ARVO-SX5. The amount of anti-human TF antibody in the culture supernatant was calculated from the value of the anti-human TF antibody (Lot No. 00C01) seeded for the calibration curve.

As shown in Table 1, direct ELISA confirmed concentration and total expression level of anti-TF antibody of about 65 to about 100 ng/ml and about 3 to about 5 μg, respectively.

TABLE 1

| | Concentration (ng/ml) | Volume (ml) | Total expression level (μg) |
|---|---|---|---|
| Original | 98.710 | 50 | 4.9 |
| N28D | 84.535 | 50 | 4.2 |
| N51D | 75.634 | 50 | 3.8 |
| N55D | 77.956 | 50 | 3.9 |
| N51D/N55D | 68.387 | 50 | 3.4 |

4. Purification of Each Anti-human TF Mutant Antibody

Each mutant was purified from 50 ml of the recovered culture supernatant using affinity chromatography (Protein A) and anion exchange chromatography (Mono Q).

4-1 Affinity Chromatography

Affinity chromatography was performed under the following conditions:

System: SMART™ System (Amersham Pharmacia Biotech)

Column: HiTrap™ Protein A HP (0.7 cm φ×2.5 cm, 1 ml, Amersham Pharmacia Biotech)

Equilibrating Buffer: D-PBS (−)

Washing Buffer: 10 mM Sodium phosphate buffer (pH 7.4)

Elution Buffer: 50 mM Acetic acid (pH 2 to 3)

After adjusting the pH to 7.4 with 0.5 M sodium monophosphate solution, a sample was concentrated 5-fold with Centriprep-50™ (Millipore, Billerica, Mass.) and loaded at a flow rate of 1 ml/min onto the column equilibrated with 10 ml (10 C.V.) equilibrating buffer. The column was washed with 5 ml (5 C.V.) washing buffer at a flow rate of 0.5 ml/min, eluted with 5 ml (5 C.V.) elution buffer, and then collected as ten fractions, each containing 0.5 ml solution. Four fractions containing the antibody were combined and neutralized to pH 6 to 7 with 0.1 ml of 1 M Tris base.

4-2 Anion Exchange Chromatography

Next, anion exchange chromatography was performed under the following conditions:

System: SMART™ System (Amersham Pharmacia Biotech)

Column: Mono Q™ PC 1.6/5 (0.16 cm φ×5 cm, 0.1 ml, Amersham Pharmacia Biotech)

Buffer A: 50 mM Tris-HCl (pH 8.0)

Buffer B: 50 mM Tris-HCl (pH 8.0)/0.5 M NaCl

Sample was prepared by adding 0.1 ml of 1 M Tris base to the Protein A elution fraction obtained by affinity chromatography to adjust the pH to 8 to 9. The sample was loaded onto the column at a flow rate of 200 μl/min, and then eluted by gradient elution using a gradient program of 0% B/5 min, 0 to 60% B/30 min, 60 to 100% B/10 min and 100% B/10 min, with a flow rate of 50 μl/min. The eluate was collected as 50 μl fractions, and 2 to 4 fractions containing the antibody were combined and subjected to activity measurement.

The affinity chromatography and anion exchange chromatography resulted in 0.5 to 1.0 μg of antibody. The anion exchange chromatogram of each mutant is shown in FIGS. 3 to 5 and the superposed chromatograms of the mutants are shown in FIG. 6. In addition, the amount and recovery rate of the proteins are shown in Table 2. The N55D mutant and N51D/N55D double mutant were obtained as almost a single peak. However, subpeaks were observed for the original anti-human TF antibody, the N51D mutant and the N28D mutant. Particularly, the N51D mutant showed 2 subpeaks, both with high contents.

TABLE 2

| | Peak No. | Initial protein amount (μg) | Concentration (ng/ml) | Volume (ml) | Total protein amount (μg) | Recovery (%) |
|---|---|---|---|---|---|---|
| Original | 1 | 4.9 | 6969.568 | 0.10 | 0.70 | 16.5 |
| | 2 | | 734.883 | 0.15 | 0.11 | |
| N28D | 1 | 4.2 | 5436.713 | 0.15 | 0.82 | 20.7 |
| | 2 | | 320.086 | 0.15 | 0.05 | |
| N51D | 1 | 3.8 | 2643.388 | 0.15 | 0.40 | 18.2 |
| | 2 | | 2724.396 | 0.10 | 0.27 | |
| | 3 | | 143.479 | 0.15 | 0.02 | |
| N55D | | 3.9 | 2811.046 | 0.20 | 0.56 | 14.4 |
| N51D/N55D | | 3.4 | 5255.977 | 0.20 | 1.05 | 30.9 |

5. Measurement of TF Binding Activity

TF binding activity was measured by competitive ELISA using biotinylated anti-human TF antibody. Each of the anti-human TF mutant antibodies was expressed in COS-7 and purified using protein A affinity chromatography and anion exchange chromatography to be used as samples. The sub-peaks observed during anion exchange chromatography of the original anti-human TF antibody, N28D mutant and N51D mutant were used for the measurement. Lot No.00C01 was used as the anti-human TF antibody standard.

shTF was adjusted to 20 nM with coating buffer (hereafter, indicated as CB), dispensed at 100 μl/well into a 96-well plate and incubated at 4° C. overnight. Each well was washed three times with rinse buffer (hereafter, indicated as RB); 200 μl dilution buffer (hereafter, indicated as DB) was added to each well. The plate was left standing at room temperature for 2 hours for blocking. After discarding DB, a 100 μl sample diluted by 2-fold serial dilution with DB containing 10,000-fold diluted biotinylated anti-human TF antibody was added to each well, and the plate was left standing at room temperature for one hour. The plate was washed three times with RB. After 100 μl ALP-streptavidin diluted 5,000-fold with DB was dispensed to each well, the plate was left standing for 1 hour at room temperature. Each well was washed 5 times with RB, and SIGMA104 adjusted with substrate buffer (hereafter, indicated as SB) to 1 mg/ml was dispensed to each well. Plates were left standing for 30 min at room temperature for color development and measured with a microplate reader at a wavelength of 405 nm and a control wavelength of 655 nm.

The assessment of binding activity was performed as follows: a straight-line as the standard was obtained by linear-regression of the concentration (logarithmic conversion value)-absorbance of the original anti-TF human antibody. The absorbance of each sample within the range of 62.5 to 500 ng/ml was converted to standard antibody concentration (Cc) using this standard straight-line. Cc (Ca) was divided by the antibody concentration to obtain the sample concentration ratio to the standard antibody that shows the same binding. This was taken as the binding activity.

Figure 7:
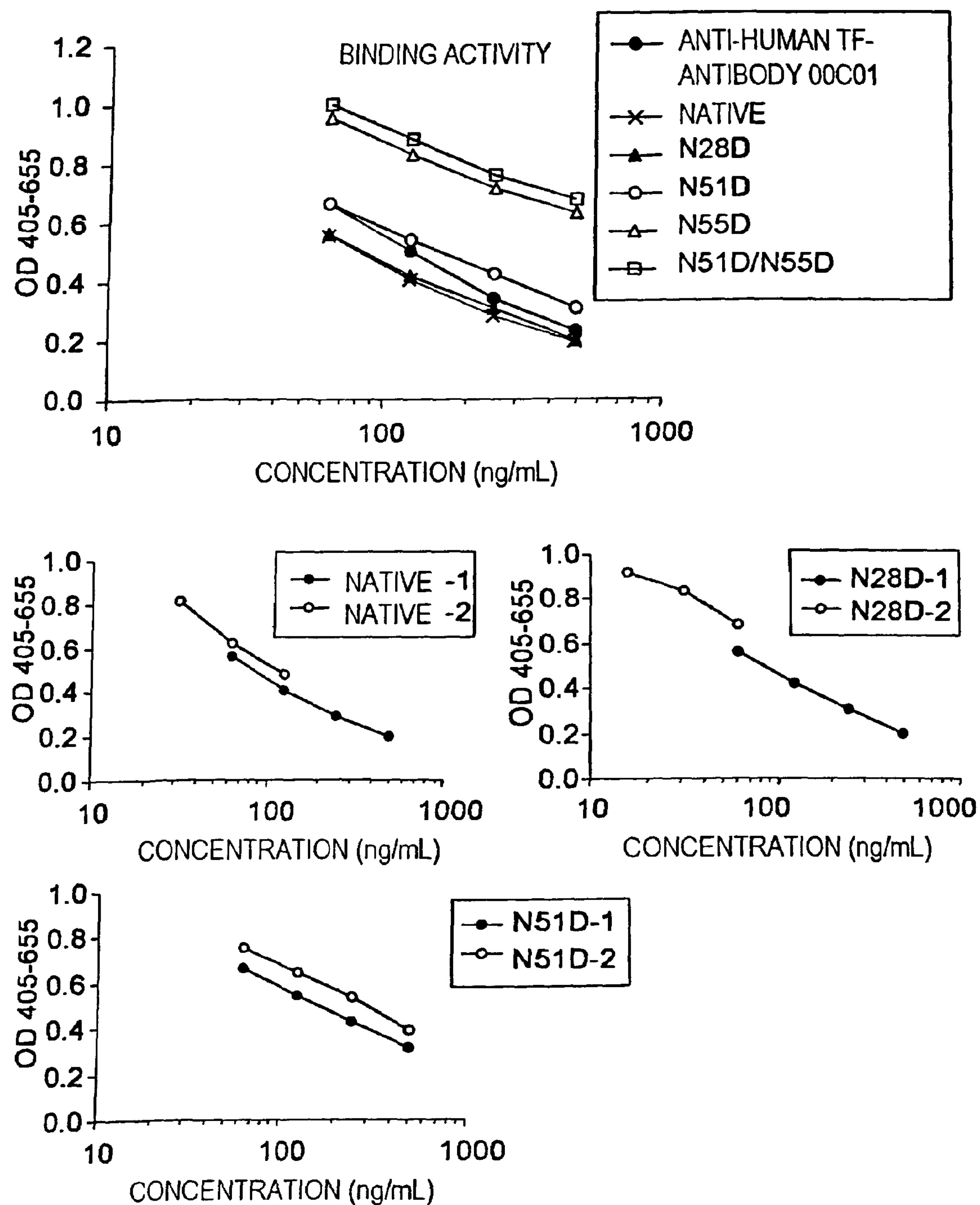
FIG. 7 depicts the binding activity of each of the anti-human TF mutant antibodies and the original anti-human TF antibody.

The results of measuring the binding activities are shown in FIG. 7 and Table 3. The binding activity of each mutant was lower than that of the original anti-human TF antibody. The binding activity of the mutant (N55D mutant) of Asn55 located in CDR2 (the Asn most likely to undergo deamidation) decreased to about 10% of the activity of the original anti-human TF antibody. The binding activity of the mutant (N51D mutant) of Asn51 (also located in CDR2) was about 50% of that of the original anti-human TF antibody, a degree of decrease smaller than observed with the N55D mutant. The N51D/N55D double mutant, a mutant of both the amino acids Asn51 and Asn 55, had a decrease in binding activity greater than that of the N55D mutant. On the other hand, the binding activity of the mutant (N28D mutant) of Asn28 located in FR1 was about 94% of the original anti-human TF antibody, showing only a slight decrease. From these findings, deamidation of Asn51 and Asn55 located in CDR2, particularly Asn55, can be expected to greatly reduce the binding activity.

Furthermore, the comparison of the binding activity of the subpeaks (peak 2) observed in the original anti-human TF antibody, N28D mutant and N51D mutant to that of the main peak (peak 1) revealed lower binding activity in all the subpeaks, compared to the main peaks.

TABLE 3

| | Binding Activity | |
|---|---|---|
| | Peak 1 | Peak 2 |
| Native | 100% | 70.6% |
| N28D | 93.9% | 46.3% |
| N51D | 49.2% | 29.0% |
| N55D | 9.2% | |
| N51D/N55D | 7.0% | |

6. Measurement of TF Neutralizing Activity

TF neutralizing activity was measured using hTF (Thromborel S), Factor VIIa and Factor X. Similar to the measurement of the binding activity, each of the anti-human TF mutant antibodies was expressed in COS-7 cells and purified using Protein A affinity chromatography and anion exchange column chromatography. Lot No.00C01 was used for the anti-human TF antibody standard.

Coagulation factor VIIa and Thromborel™ S were diluted with assay buffer (TBS (pH 7.49) containing 5 mM $CaCl_2$ and 0.1% BSA; hereafter, indicated as AB) to 0.1 PEU/ml and 120-fold (v/v), respectively. 60 μl of these mixtures were dispensed to each well of a plate and left standing for 60 min at room temperature. ABX (wherein Factor X is diluted with AB to 0.25 PEU/ml) was used to dilute the samples, and 40 μl of sample diluted to the desired concentration was dispensed to each well of the plate. The plate was left standing for 30 min at room temperature, and the reaction was quenched by adding 10 μl/well of 500 mM EDTA. S-2222 mixture was prepared by mixing one volume of S-2222, a chromogenic substrate, solution with one volume of MilliQ™ $H_2O$ and two volumes of 0.6 mg/ml hexamethylene bromide solution. Fifty μl/well of the S-2222 mixture was dispensed into the plate and left standing at room temperature. After 30 min, measurements were performed using a micro plate reader at a measurement wavelength of 405 nm and a control wavelength of 655 nm.

Figure 8:
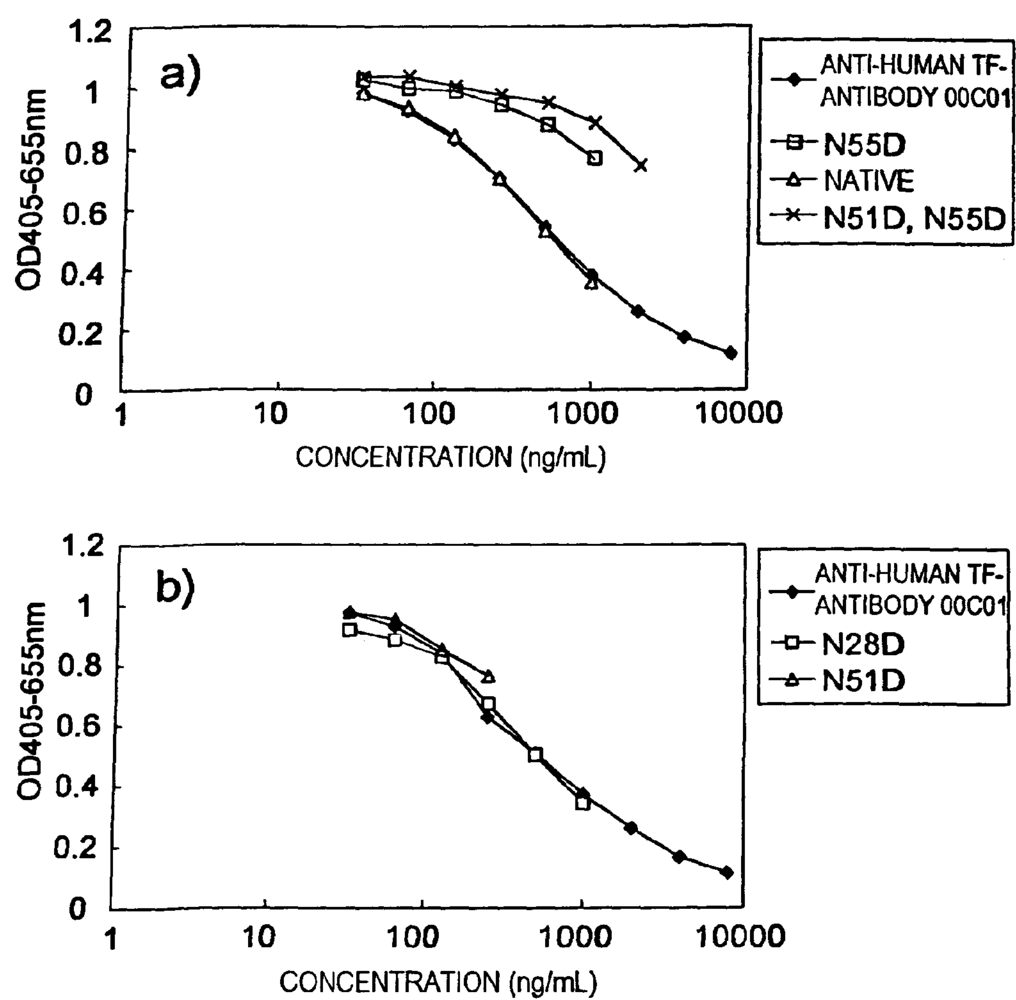
FIGS. 8A-B depict the neutralizing activity of each of the anti-human TF mutant antibodies and the original anti-human TF antibody.

Measurement results on the neutralizing activity are shown in FIG. 8 and Table 4. The concentration of each of the mutants was calculated using the anti-human TF antibody as a standard, and the neutralizing activity ratio compared to the anti-human TF antibody standard was obtained. The neutralizing activity ratio was based on a concentration of 250 ng/ml, at which concentration all samples could be measured. The original anti-human TF antibody and N28D mutant retained a neutralizing activity almost equivalent to the anti-human TF antibody standard. Thus, the deamidation of Asn28 located in FR was considered not to decrease neutralizing activity.

On the other hand, the neutralizing activity ratios of the N51D and N55D mutants compared to the anti-human TF antibody standard decreased to 65.6% and 19.9%, respectively. Therefore, the deamidation of Asn51 and Asn55 located in a CDR of the anti-human TF antibody was strongly suggested to cause a decrease of neutralizing activity.

TABLE 4

| | Added concentration (ng/ml) | Calculated concentration (ng/ml) | Neutralizing activity ratio (%) |
|---|---|---|---|
| N28D | 250 | 253 | 101 |
| N51D | 250 | 164 | 65.6 |
| N55D | 250 | 49.8 | 19.9 |
| N51D/N55D | 250 | 31.3 | 12.5 |
| Native | 250 | 248 | 99.1 |

From the results described above, the solution pH-dependent decrease in TF-binding activity and increase in low pI molecular species of unformulated anti-human TF antibody under antibody destabilizing conditions were revealed to result mainly from the deamidation of Asn55 in the CDR2 region.

Example 2

Measurement of TF Binding and Neutralizing Activities of Gly56 Substitution Mutant of Anti-human TF Antibody The anti-human TF antibody described in WO 99/51743 contains the humanized heavy chain version i (SEQ ID NO: 25, FIG. 1) and the humanized light chain version b2 (SEQ ID NO: 26, FIG. 1). Based on its amino acid sequence, mutants were prepared wherein the Gly56 in the heavy chain CDR2 that is considered as an important amino acid in the construction of the loop of CDR2 had been substituted with 19 other amino acids. Then, the TF-binding activity of each mutant was measured. Furthermore, neutralizing activity and deamidation was observed for the mutants wherein Gly56 had been substituted with Ile, Leu, Phe, Glu or Lys.

The amino acid sequence of the antibody follows the sequence described by Kabat et al. (Kabat E. A., Wu T. T., Perry H. M., Gottesman K. S. and Foeller C., "Sequences of proteins of immunological interest. 5th ed.", US Dept. Health and Human Services, Bethesda, Md., 1991).

1. Construction of Anti-human TF Mutant Antibody Expression Vector

The cloning vector pCVIDEC-AHi (FIG. 9A) and the anti-human TF antibody expression vector pN5KG4P-AHi-ALb2 carrying the heavy chain variable region (AHi) of the anti-human TF antibody were isolated from *E. coli* SCS110 ($dam^-/dcm^-$).

The substitution of the codon encoding Gly56 with a codon encoding a different amino acid was performed on pCVIDEC-AHi. In this procedure, the substitution with any of 15 amino acids wherein the third nucleotide of the codon can be fixed to "C" was performed as follows: digesting a fragment of about 30 up comprising the coding region of Asn55-Gly56 at the unique sites XbaI and BalI of pCVIDEC-AHi, and integrating a fragment prepared using a synthetic olio DNA wherein the 2 nucleotides at the 3'-end of the Gly56-coding codon been randomized (FIG. 9B). The XbaI-BalI fragment was prepared by elongating the 3'-end with two nucleotides using Vent polymerase (NEB, Inc.) so that the 1st and 2nd nucleotides of the Gly56 codon in the CDR2 variable region of the anti-human TF antibody heavy chain region become random nucleotide sequences, and then digesting with XbaI. This procedure was believed to enable production of 15 mutants with high codon usage in mammals via one operation. However, in fact, only 8 kinds of mutants were produced since optimal reaction conditions could not be found. Therefore, the remaining mutants were constructed using other restriction enzyme sites.

Mutants comprising substitution of an amino acid wherein the $3^{rd}$ nucleotide of the codon for Gly56 has to be converted, as well as those that could not be produced by the above-descried method, were produced as follows: a vector wherein the EcoRI site of pCVIDEC-AHi is changed to HindIII site was constructed and digested at the unique sites ApoI and XbaI of pCVIDEC-AHi, and a fragment produced using synthetic olio DNA was inserted. That is, apart from the XbaI and BalI sites, ApoI and XbaI sites were the possible sites that can be used as the restriction enzyme sites. However, ApoI also digests the EcoRI sites in the vector. Therefore, the EcoRI site was first removed by changing it to a HindIII site. The ApoI-XbaI fragment was about 55 bp. Thus, a synthetic olio DNA was prepared so that a total of about 16 bp overlapped upstream and downstream of the nucleotide sequence of the codon encoding Gly 56. After annealing, the fragment was elongated using Vent polymerase and digested with ApoI and XbaI (FIG. 9C and Table 5).

TABLE 5

| EcoRI site deletion adapter | Hind III | |
|---|---|---|
| G AATTC | AATTGGAAGCTTGC | (SEQ ID NO: 1) |
| CTTAA G | CCTTCGAACGTTAA | (SEQ ID NO: 2) |
| H-G56M primer-F | GAGTCTAGAATGGATTGGTGGGAATGATCCTGCGAATATGC | (SEQ ID NO: 3) |
| H-G56M primer-R | GAGAATTTCGGGTCATACATACTATGCATATTCGCAGGAT | (SEQ ID NO: 4) |
| H-G56K primer-F | GAGTCTAGAATGGATTGGTGGGAATGATCCTGCGAATAAGCAT | (SEQ ID NO: 5) |

TABLE 5-continued

| EcoRI site deletion adapter | Hind III | |
|---|---|---|
| H-G56K primer-R | GAGAATTTCGGGTCATACATACTATGCTTATTCGCAGGAT | (SEQ ID NO: 6) |
| H-G56W primer-F | GAGTCTAGAATGGATTGGTGGGAATGATCCTGCGAATTGGCAT | (SEQ ID NO: 7) |
| H-G56W primer-R | GAGAATTTCGGGTCATACATACTATGCCAATTCGCAGGAT | (SEQ ID NO: 8) |
| H-G56Q primer-F | GAGTCTAGAATGGATTGGTGGGAATGATCCTGCGAATCAGCAT | (SEQ ID NO: 9) |
| H-G56Q primer-R | GAGAATTTCGGGTCATACATACTATGCTGATTCGCAGGAT | (SEQ ID NO: 10) |
| H-G56E primer-F | GAGTCTAGAATGGATTGGTGGGAATGATCCTGCGAATGAGCAT | (SEQ ID NO: 11) |
| H-G56E primer-R | GAGAATTTCGGGTCATACATACTATGCTCATTCGCAGGAT | (SEQ ID NO: 12) |
| H-G56F primer-F | GAGTCTAGAATGGATTGGTGGGAATGATCCTGCGAATTTCCAT | (SEQ ID NO: 13) |
| H-G56F primer-R | GAGAATTTCGGGTCATACATACTATGGAAATTCGCAGGAT | (SEQ ID NO: 14) |
| H-G56T primer-F | GAGTCTAGAATGGATTGGTGGGAATGATCCTGCGAATACCCAT | (SEQ ID NO: 15) |
| H-G56T primer-R | GAGAATTTCGGGTCATACATACTATGGGTATTCGCAGGAT | (SEQ ID NO: 16) |
| H-G56N primer-F | GAGTCTAGAATGGATTGGTGGGAATGATCCTGCGAATAACCAT | (SEQ ID NO: 17) |
| H-G56N primer-R | GAGAATTTCGCGTCATACATACTATGGTTATTCGCAGGAT | (SEQ ID NO: 18) |
| H-G56D primer-F | GAGTCTAGAATGGATTGGTGGGAATGATCCTGCGAATGACCAT | (SEQ ID NO: 19) |
| H-G56D primer-R | GAGAATTTCGGGTCATACATACTATGGTCATTCGCAGGAT | (SEQ ID NO: 20) |
| H-G56P primer-F | GAGTCTAGAATGGATTGGTGGGAATGATCCTGCGAATCCCCAT | (SEQ ID NO: 21) |
| H-G56P primer-R | GAGAATTTCGGGTCATACATACTATGGGGATTCGCAGGAT | (SEQ ID NO: 22 |
| H-G56C primer-F | GAGTCTAGAATGGATTGGTGGGAATGATCCTGCGAATTGCCAT | (SEQ ID NO: 23) |
| H-G56C primer-R | GAGAATTTCGGGTCATACATACTATGGCAATTCGCAGGAT | (SEQ ID NO: 24) |

Primers for the construction of anti-human TF mutant antibodies using XbaI and ApoI sites are shown.

In addition, the nucleotide sequences indicated in Table 5 are shown in SEQ ID NOs: 1 to 24.

The sequences of the constructs encoding 19 different anti-human TF mutant antibodies were confirmed in the cloning vector by a sequencer. Furthermore, the sequences were reconfirmed after constructing mutant expression vectors by replacing the heavy chain variable region obtained through NheI and SalI digestion with the heavy chain variable region digested from the anti-human TF antibody expression vector with NheI and SalI. After confirming that the target sequence was obtained, the anti-human TF mutant antibody expression vector was amplified using *E. coli* DH5α and purified using a QIAGEN Maxi™ column, and the sequence was confirmed. As a result, 19 different anti-human TF mutant antibody expression vectors were obtained.

2. Transient Expression of Anti-human TF Mutant Antibody in CHO Cells

A total of 20 expression vectors, i.e., the constructed anti-human antibody heavy chain Gly56 mutant expression vectors and Gly56 non-substituted antibody (Gly56Gly) expression vector, were transfected into CHO cells via the lipofection method for transient expression. A day before lipofection, the CHO (dhfr−) cells were cultured on 10% FCS-α-MEM in an atmosphere of 5% $CO_2$ at 37° C. The CHO cells were seeded at 33 $10^5$ cells/well on 12-well plates and cultured at 5% $CO_2$ at 37° C.

After 6 μl of FuGENE6™ Transfection Reagent (Boehringer Mannheim GmbH) were added to 100 μl of Opti-MEM™ (GIBCO BRL) and the mixture was left standing for 5 min, the mixture was added to tubes, each of which contained 1 μg of one of the anti-human TF antibody heavy chain Gly56 mutant expression vectors pN5KG4P-AHi-A1b2-G56X (X: each of 20 different amino acids). Each tube was left standing for 20 min to form a FuGENE6/DNA complex. After discarding the media of the CHO cells seeded on the previous day, 2 ml/well of 10% FCS-α-MEM was newly added followed by the addition of each FuGENE6/DNA complex in triplicate.

The cells were cultured at 37° C. at 5% $CO_2$ for one day and then washed with PBS. Media were replaced by adding 3 ml/well of 10% FCS-α-MEM. After a 7-day incubation at 5% $CO_2$ at 37° C., about 9 ml of culture supernatant containing each of the anti-human TF mutant antibodies was transferred into a 15 ml tube, centrifuged at 1000 rpm for 5 min, and concentrated to 10-fold through ultrafiltration. The obtained culture supernatant was used as the anti-human TF antibody heavy chain Gly56Xaa mutant sample.

3. Measurement of TF Binding Activity

Human IgG content in the anti-human TF antibody heavy chain Gly56Xaa mutant samples was measured to adjust the IgG concentration of each sample to 100 ng/ml.

TF binding activity was measured by competitive ELISA using biotinylated anti-human TF antibody. shTF was adjusted to 20 nM with CB, dispensed at 100 μl/well into a 96-well plate, and left standing at 4° C. overnight. The plate was washed three times with RB and 200 μl/well of DB was dispensed thereto; then the plate was left standing for blocking at room temperature for 2 hours. After removing DB, 100

μl/well of standard or sample diluted by 2-fold serial dilution with DB containing biotinylated anti-human TF antibody (diluted 10,000-fold at final concentration) was added. The plates were left standing at room temperature for 1 hour. After washing 3 times with RB, 100 μl/well of ALP-streptavidin, diluted 8,000-fold with DB, was added and left standing at room temperature for one hour. SIGMA104™ adjusted to 1 mg/ml with SB was added after washing 3 times with RB, and left standing for about 20 min at room temperature to develop colors. The absorbance was measured with a microplate reader at a wavelength of 405 nm and a control wavelength of 655 nm.

The binding activity was compared by determining the concentration that showed 50% activity according to the following procedure: the absorbance at each measured point was converted to percentage (%) by taking the absorbance of sample (−) and biotinylated antibody (+) as 100%. A linear regression equation of "concentration (logarithmic conversion value)−absorbance (%)" was obtained based on two points which sandwich the 50% value of each sample. Then, the concentration giving 50% absorbance was calculated to calculate the binding activity of each sample from Equation 1.

binding activity=(50% activity concentration of the standard antibody)/(50% activity concentration of sample)×100 Equation 1

Figure 10:
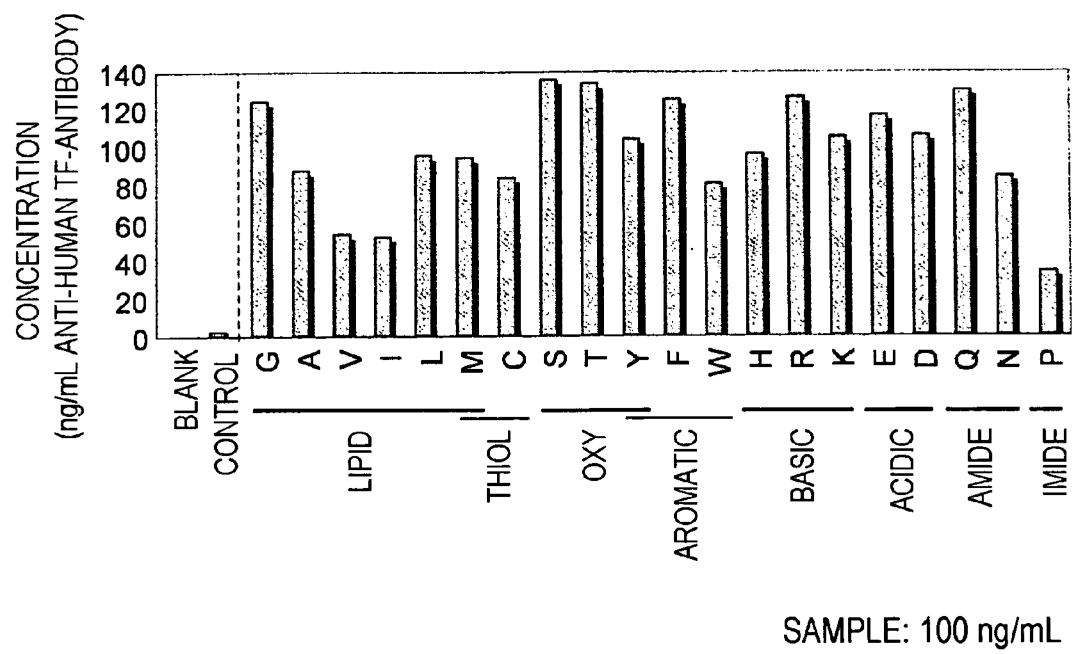
FIG. 10 depicts a graph comparing the binding activity of each of the anti-human TF mutant antibodies. The anti-human TF antibody concentration conversion values calculated based on the calibration curve plotted using the bulk anti-human TF antibody (Lot No. 00C01) are shown. Blank: 10% FCS-α-MEM culture medium; control: CHO cell culture supernatant; G to P: each of the anti-human TF antibody heavy chain Gly56 mutants.

The anti-human TF antibody concentration conversion value that was calculated based on the calibration curve produced using bulk anti-human TF antibody (Lot No.00C01) is shown in FIG. 10. The Gly56 non-substituted antibody (Gly56Gly) expressed in CHO cells retained a TF binding activity almost equivalent to the bulk anti-human TF antibody. A decrease in binding activity was observed in the Gly56 mutants, Gly56Val, Gly56Ile and Gly56Pro.

The following assay was performed to examine the TF binding activity of the anti-human TF antibody heavy chain Gly56 mutants in detail. Specifically, the TF binding activity was measured by a competitive ELISA method using the anti-human TF mutant antibodies by changing the amount of added sample within the range of 25 to 200 ng/ml. Measurements on Gly56Asn and Gly56Asp were not performed due to the lack of sample amount.

Figure 11:
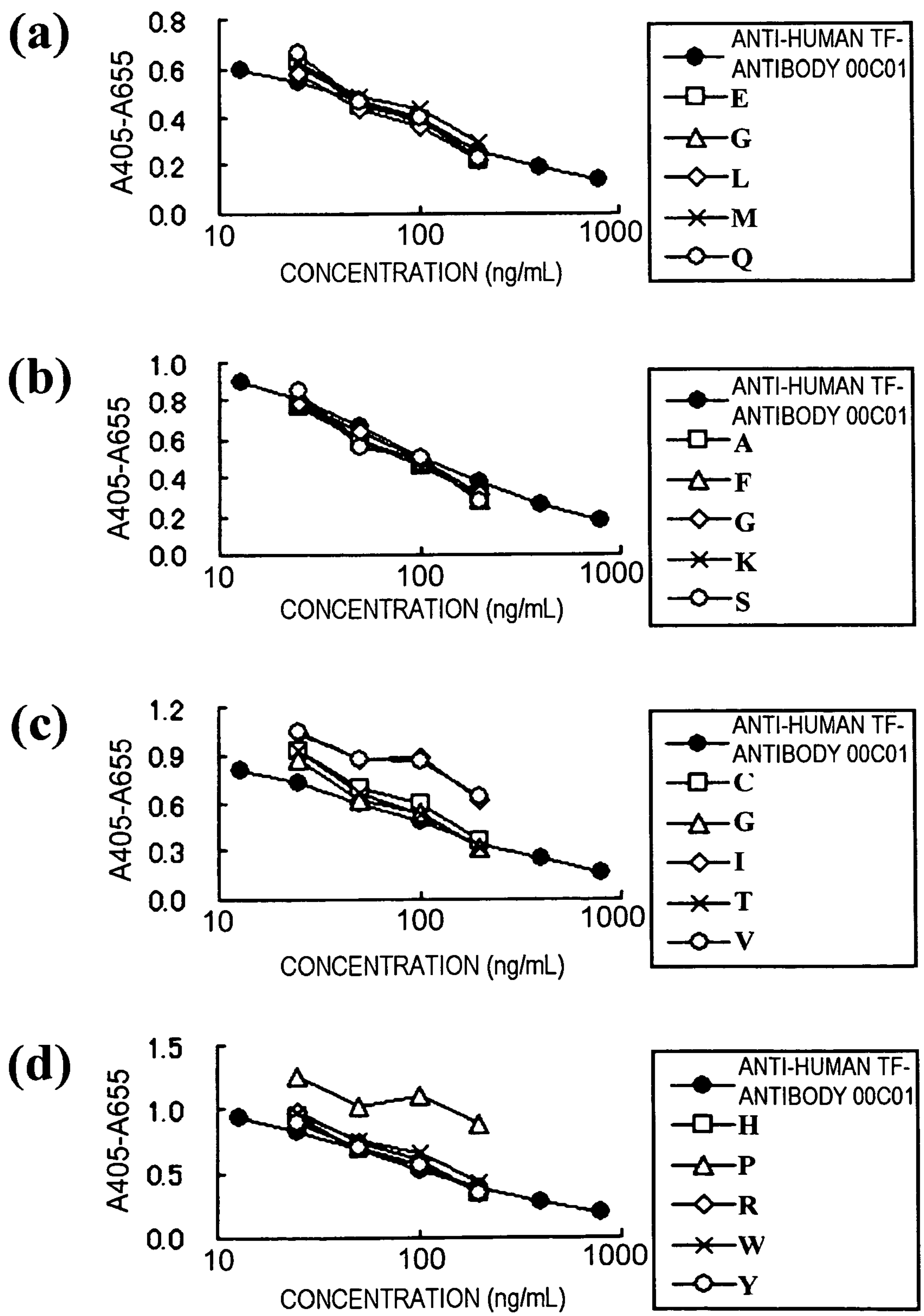
FIGS. 11 A-D depict the binding activity of each of the anti-human TF mutant antibodies mutants.

The measurement results are shown in FIG. 11. Among the examined 18 anti-human TF antibody heavy chain Gly56 mutants, the TF binding activity of each of Gly56Val, Gly56Ile and Gly56Pro was significantly decreased compared with the bulk anti-human TF antibody (Lot No.00C01) and Gly56 non-substituted antibody (Gly56Gly). However, no significant difference in the TF binding activity could be observed for the other 15 mutants. Thus, the TF binding activity was apparently maintained even after substituting the Gly56 with another amino acid.

4. Measurement of TF Neutralizing Activity

Coagulation factor VIIa and Thromborel S™ were diluted with AB to 0.1 PEU/ml and 120-fold (v/v), respectively. Sixty μl/well of a mixture thereof was dispensed to a plate and left standing at room temperature for 60 min. Twenty μl/well of sample diluted by 2-fold serial dilution with 10 mM phosphate buffer was dispensed followed by 20 μl/well coagulation factor (Factor X) solution diluted to 0.5 PEU/ml with AB (supplemented with $CaCl_2$ solution to a $CaCl_2$ concentration of 10 mM). The plate was left standing at room temperature for 30 min, and then the reaction was quenched by adding 10 μl/well of 500 mM EDTA. Fifty μl/well of a solution of test-team chromogenic substrate S-2222 solution and polybrene solution mixed at 1:1 was dispensed and left standing at room temperature. After 30 min, measurements were taken by a microplate reader at a measurement wavelength of 405 nm and a control wavelength of 655 nm.

The neutralizing activity was compared by determining the concentration showing 50% activity according to the following procedure: the absorbance at each measured point was converted to percentage (%) by taking the absorbance of sample (−) and coagulation factor X (+) as 100%, and sample (−) and coagulation factor X (−) as 0%. A linear regression equation of "concentration (logarithmic conversion value)−absorbance (%)" was obtained based on two points that sandwich the 50% value of each sample. Then, the concentration giving 50% absorbance was calculated to calculate the neutralizing activity of each sample from Equation 2.

Neutralizing activity (IC50)=(50% activity concentration of the standard antibody)/(50% activity concentration of sample)×100 Equation 2

5. Construction of Stable Expression System of Anti-human TF Mutant Antibodies Using CHO Cells Five kinds of mutants, Gly56Leu, Gly56Phe, Gly56Glu, Gly56Lys and Gly56Ile, wherein the Gly56 is substituted to Leu (aliphatic amino acid), Phe (aromatic amino acid), Glu (acidic amino acid), Lys (basic amino acid) and Ile (branched-chain aliphatic amino acid), respectively, were produced in sufficient quantity to compare the activity of the anti-human TF mutant antibodies by constructing stable expression cell lines.

5-1 Gene Transfer Into CHO Cells

CHO (dhfr−) cells were washed with PBS and then resuspended in PBS to about $1\times10^7$ cells/ml. The cells were transferred into a 0.4 cm cuvette together with 10 μg of the expression vector of anti-human TF antibody heavy chain Gly56 mutant, pN5KG4P-AHi-A1b2-G56X. Electroporation was performed at 1.5 kV with 25 μF. After standing for 10 min, the cells were suspended in 200 ml of 10% FCS-α-MEM nucleic acid (−) media. Two hundred μl/well of the suspension was seeded and cultured on ten 96-well plates.

5-2 Selection of Transfected Cells

The amount of expressed antibody in wells wherein cell growth could be observed during the 96-well plate culture was compared by hIgG ELISA. Cells that showed high hIgG expression were subcultured from 10 wells each at a total of 70 wells into 12 well plates and cultured in 10% FCS-α-MEM nucleic acid (−) media. The expression amount of anti-human TF mutant antibody was measured by hIgG ELISA at the time when the cells had acclimatized to the 10% FCS-α-MEM nucleic acid (−) media and showed satisfactory growth. Four wells were selected for each mutant and subcultured into a 50 ml flask. Antibody production was enhanced by replacing the media with 10% FCS-α-MEM nucleic acid (−) containing 10 nM MTX.

5-3 Production of Anti-human TF Mutant Antibody by Large-Scale Culture Using Serum Free Media Among the anti-human TF mutant antibody clones, one clone each for each mutant having a high hIgG expression level was selected and cultured in six 175 $cm^2$ flasks using media containing 10 nM MTX. The media were replaced with 150 ml CHO—S—SFM II serum free media after reaching subconfluence and incubated for 7 days. The culture supernatant was collected, treated with 0.22 μm filter, and stored at −80° C. until purification.

5-4 Measurement of Expression Level of Anti-human TF Mutant Antibody by Sandwich ELISA One hundred μl/well of anti-human IgG (γ) antibody was dispensed into a 96-well plate and left standing at 4° C. overnight. After washing 3 times with RB, 200 μl/well of DB was dispensed and left standing at room temperature for 2 hours for blocking. After the DB was discarded, 100 μl/well of the standard or sample that was properly diluted with DB or medium used to recover the antibody from the anti-human TF mutant antibody producing cells was added and left standing at room temperature for 2 hours. After washing three times with RB, 100 μl/well of HRP-labeled anti-human IgG antibody diluted 10,000-fold with DB was dispensed and left standing at room temperature for 1 hour. After washing 10 times with RB, 100 μl/well of chromogenic reagent was dispensed and left standing at room temperature for about 10 min. Color reaction was quenched by the addition of 50 μl/well of 2 N sulfuric acid to measure the absorbance with a microplate reader at a measurement wavelength of 450 nm and a control wavelength of 655 nm.

Consequently, several milligrams of each of the anti-human TF mutant antibodies, except Gly56Gly, were obtained (Table 6).

TABLE 6

| | Version | | | | | | |
|---|---|---|---|---|---|---|---|
| | G56G | G56F | G56L | G56E | G56K | G56I | 99D01 |
| Clone No. | 196 | 41 | 96 | 23 | 237 | 127 | |
| α-MEM N(−) (ng/ml) | 29 | 64 | 9 | 59 | 600 | 110 | |
| α-MEM 10 nM MTX(ng/ml) | 50 | 836 | 3451 | 6143 | 423 | 369 | |
| CHO-SFM-II (large-Scale: 900 ml) (μg/ml) | 0.24 | 15.4 | 41.7 | 50 | 11.5 | 5.8 | |
| Purified (after buffer exchange: μg/ml, total 7 ml) | — | 319 | 379 | 624 | 180 | 153 (4 ml) | 1556 |

6. Purification of Each Anti-human TF Antibody Mutant

Each mutant was purified from the supernatant of the large scale culture containing each of the mutants using a HiTrap™ rProtein A FF column and a HiTrap Q™ Sepharose HP column.

6-1 Affinity Chromatography for Purification

Affinity chromatography was performed in a refrigerated room under the following conditions:

System: FPLC System

Column: HiTrap™ rProtein A FF (1.6 cm ϕ×2.5 cm, 5 ml)

Equilibrating buffer: D-PBS (−)

Washing buffer: 10 mM Sodium phosphate buffer (pH 7.4)

Elution buffer: 50 mM Acetic acid (pH 2 to 3)

Samples were loaded onto the column after adjusting the pH to 7.4 with 0.5 M disodium phosphate solution. Fifty ml of washing buffer was used to dilute 1.5 ml (16.5 mg) of the anti-human TF antibody standard. Elution was performed with 25 ml (5 C.V.) elution buffer at a flow rate of 5 ml/min and the pH was neutralized to 6 to 7 with 1.25 ml of 1 M Tris base.

6-2 Anion Exchange Chromatography for Purification

Next, anion exchange chromatography was conducted in a refrigerated room under the following conditions:

System: FPLC System

Column: HiTrap Q™ Sepharose HP (0.7 cm ϕ×2.5 cm, 1 ml)

Buffer A: 50 mM Tris-HCl (pH 8.0, 4° C.)

Buffer B: 50 mM Tris-HCl (pH 8.0, 4° C.)/1 M NaCl

Sample was prepared by adjusting the pH of the Protein A elution fraction obtained via affinity chromatography to 8 to 9 through the addition of 1.25 ml of 1 M Tris base. Elution steps of 0 mM NaCl (5 C.V.), 250 mM NaCl (5+5 C.V.) and 1 M NaCl (100 C.V.) at a flow rate of 1 ml/min were performed and the first half 5 C.V. (5 ml) of the 250 mM NaCl step was collected.

Five hundred μg or more of each of the anti-human TF mutant antibodies, except Gly56Gly, was obtained (Table 5). Gly56Gly was not obtained. Therefore, bulk anti-human TF antibody (Lot No.99D01) was purified according to a similar procedure to use it for comparison with anti-human TF antibody (Table 5).

7. Anion Exchange Chromatography for Analysis

Sample was analyzed by anion exchange chromatography at room temperature under the following conditions:

System: SMART™ System

Column: MonoQ PC™ 1.6/5 (0.16 cm ϕ×5 cm, 0.1 ml)

Buffer A: 50 mM Tris-HCl (pH 8.0, 20° C.)

Buffer B: 50 mM Tris-HCl (pH 8.0, 20° C.)/500 mM NaCl

Gradient elution with a gradient program of 0% B/5min, 0-60% B/30min, 60 to 100% B/10 min and 100% B/10 min at a flow rate of 50 μl/min was performed. Two μg of sample (calculated by UV conversion) was diluted 3 to 50 times with 50 μl of buffer A and 25 μl thereof was analyzed.

Figure 12:
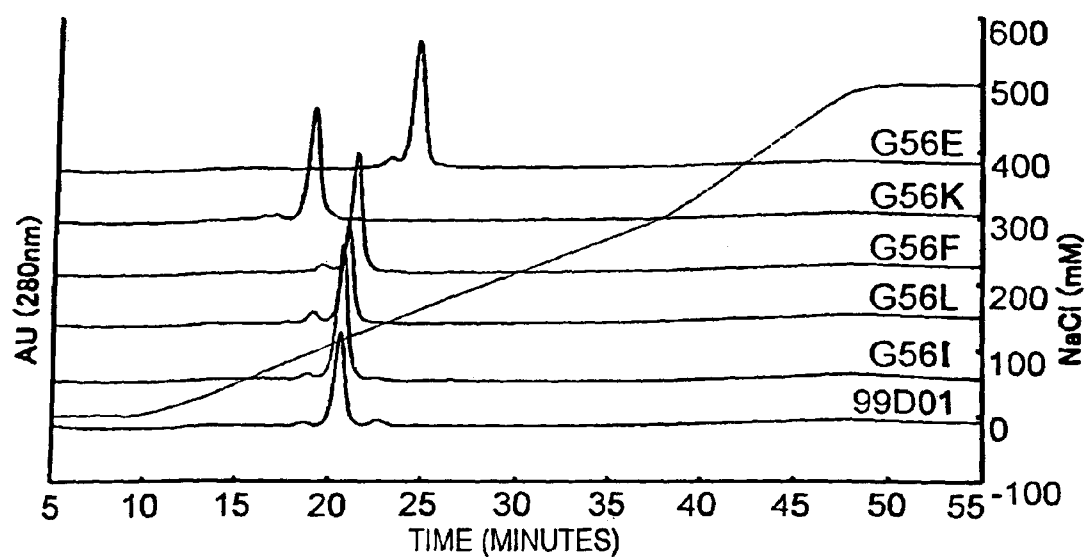
FIG. 12 depicts the elution profiles of each of the anti-human TF mutant antibodies and the bulk anti-human TF antibody (99D01).

The analysis by anion exchange chromatography of purified bulk anti-human TF antibody (99D01) and each of the anti-human TF mutant antibody revealed almost a single peak, although with a change in elution time depending on the introduced amino acid mutation (FIG. 12).

8. Suppression of Anti-human TF Antibody Deamidation by Amino Acid Mutation

In order to examine the deamidation reaction, accelerated testing was performed under heated conditions using a neutral pH buffer wherein deamidation easily occurs.

8-1 Replacement of Buffer

Replacement of sample buffer with 20 mM sodium phosphate buffer/150 mM sodium chloride (pH 7.5) buffer using a PD-10 desalting column was performed. After equilibrating the column, 2.5 ml sample was loaded onto two columns and eluted with 3.5 ml buffer.

8-2 Sample Preparation for Accelerated Testing

Each sample of the anti-human TF mutant antibodies was diluted to 100 μg/ml based on the value quantitated by hIgG ELISA. Buffer containing 20 mM sodium phosphate buffer/150 mM NaCl (pH 7.5) was used. After passing through a 0.22 μm filter, 1 ml of each sample was dispensed into a 5 ml vial.

8-3 Accelerated Testing

Accelerated testing on the purified bulk anti-human TF antibody (99D01) and anti-human TF mutant antibodies was performed for four weeks at 40° C. in 20 mM sodium phosphate buffer/150 mM NaCl (pH 7.5) solution. A portion was sampled at each time point of 0, 1, 2 and 4 weeks, and its activity was analyzed through the comparison of TF binding activity and TF neutralizing activity. Deamidation at each time point was analyzed using analytical anion exchange chromatography.

The value (Table 7) obtained by requantitation using the monomer fraction of GPC as an indicator was used for the comparison of activity. Specifically, quantitation of antibody was performed at room temperature under following conditions:

System: Waters (600S™ Controller, 616™ Pump, 486™ Tunable absorbance detector, 717 Plus™ Autosampler)

Column: TSK gel G3000SWXL (0.78 cm ϕ×30 cm, guard column 0.6 cm ϕ×4 cm)

Buffer: 50 mM Sodium phosphate/300 mM NaCl (pH 7.0)

Analysis was performed at a flow rate of 0.5 ml/min using 100 μl (equivalent to 10 μg) of accelerated material as a sample.

TABLE 7

| | Initial value | 1 week | 2 weeks | 4 weeks |
|---|---|---|---|---|
| 99D01 | 116.1 | 115.2 | 116.5 | 112.4 |
| G56L | 116.5 | 113.8 | 115.6 | 113.7 |
| G56I | 102.7 | 99.6 | 98.4 | 94.5 |
| G56F | 118.3 | 115.3 | 114.8 | 111.8 |
| G56E | 110.8 | 110.2 | 110.7 | 109.8 |
| G56K | 135.2 | 134.9 | 136.0 | 130.9 |

Figure 13:
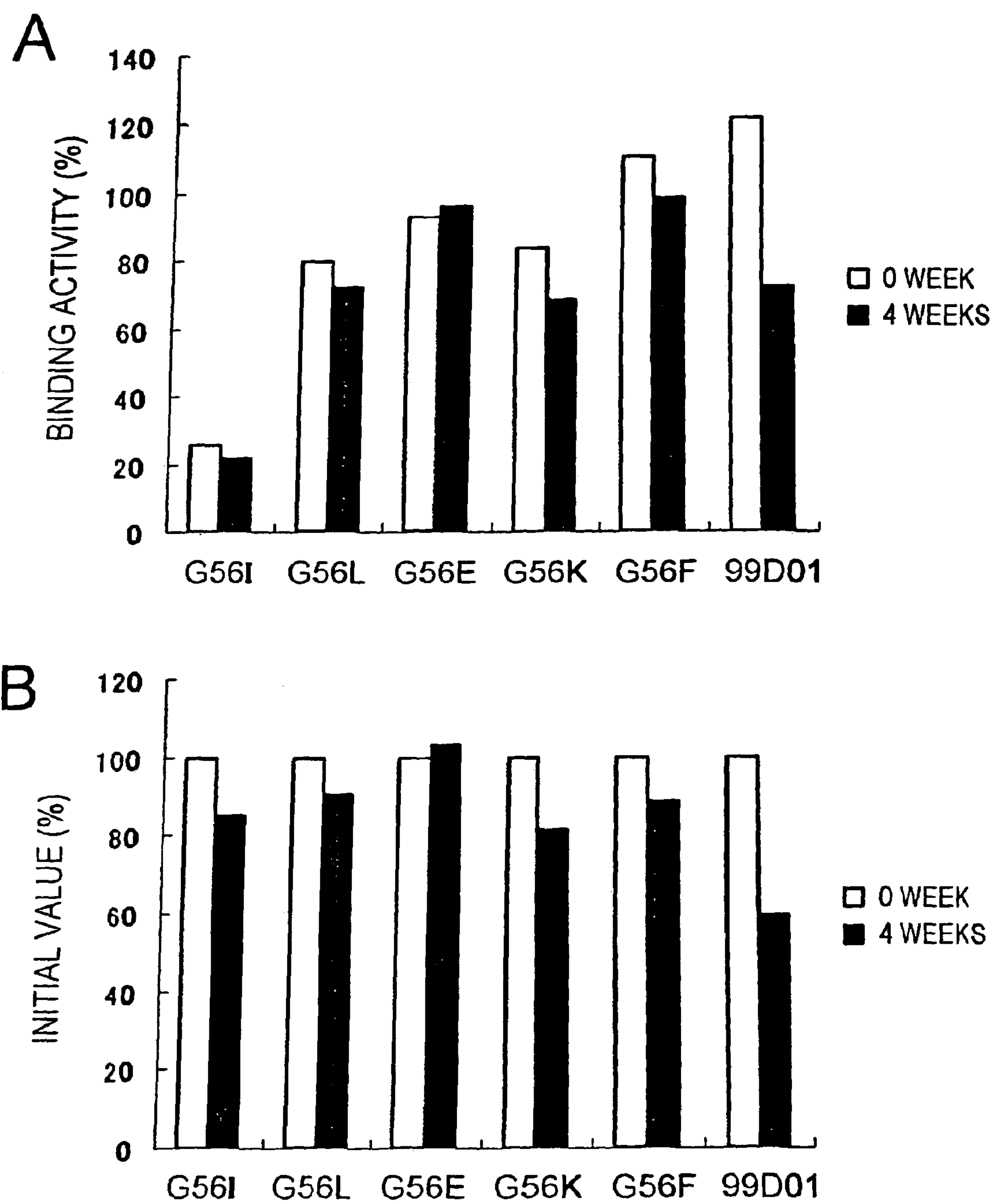
FIGS. 13A-B depict graphs showing the binding activity before and after the accelerated testing on each of the anti-human TF mutant antibodies and the bulk anti-human TF antibody (99D01), and the ratio compared with the initial value.

Similar to transiently expressed anti-human TF mutant antibodies, the result showed that the TF binding activity of Gly56Ile before the accelerated testing was about 26% of the bulk anti-human TF antibody (Lot No.00C01). Namely, the activity was low and significantly reduced compared with 99D01 (FIG. 13A). Almost an equivalent activity to 99D01 was retained by Gly56Leu, Gly56Glu, Gly56Phe and Gly56Lys (FIG. 13A). After 4 weeks of accelerated testing, each anti-human TF mutant antibody retained 80% or more of its activity before the accelerated testing, whereas the activity of 99D01 decreased to about 60% of its activity before the accelerated testing (FIG. 13B).

Figure 14:
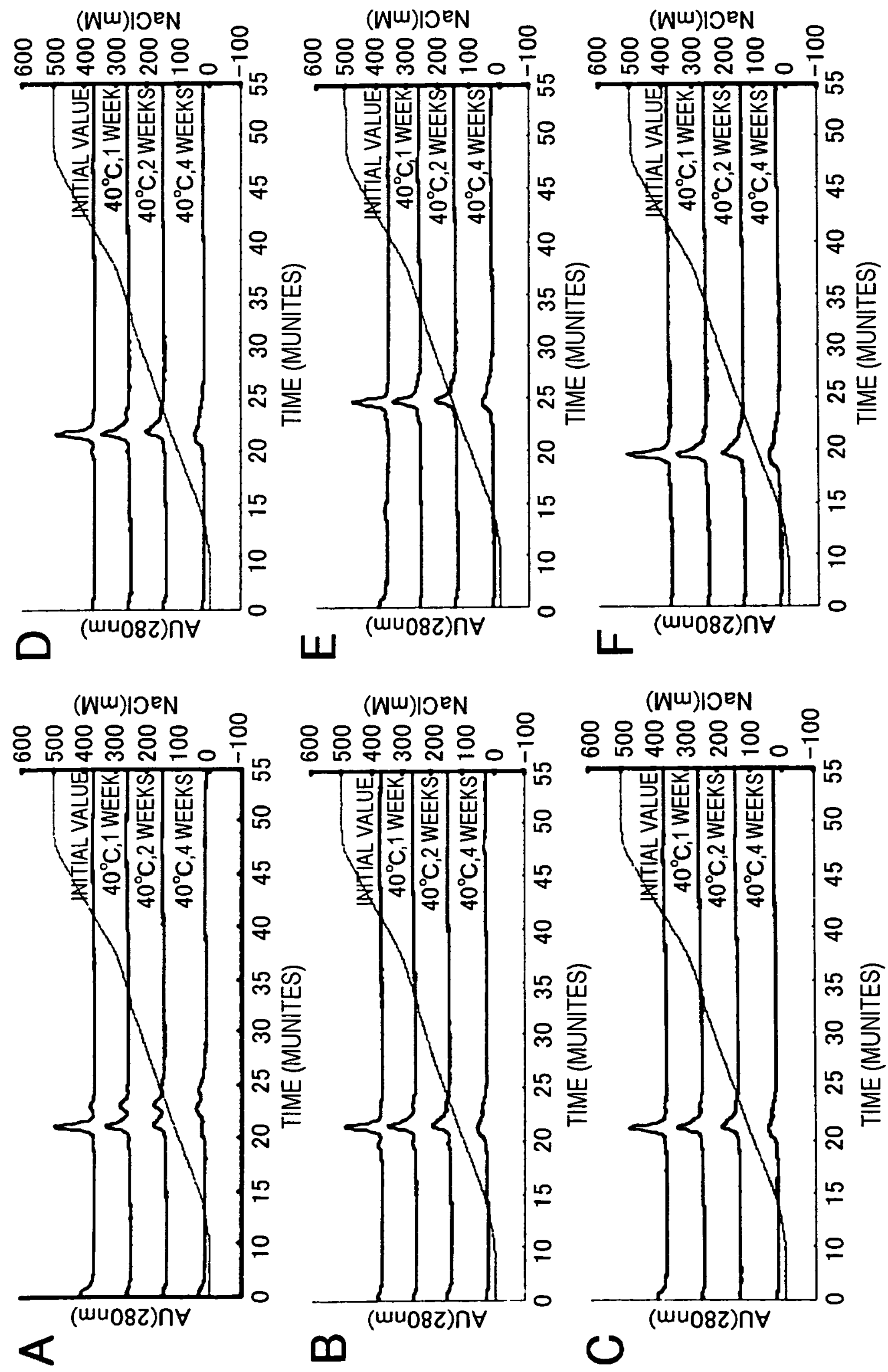
FIG. 14 depicts the anion chromatograph and neutralizing activity before and after the accelerated testing on each of the anti-human TF mutant antibodies and the bulk anti-human TF antibody (99D01). A: 99D01 (G56G); B: G56L; C: G56I; D: G56F; E: G56E; and F: G56K.
Figure 15:
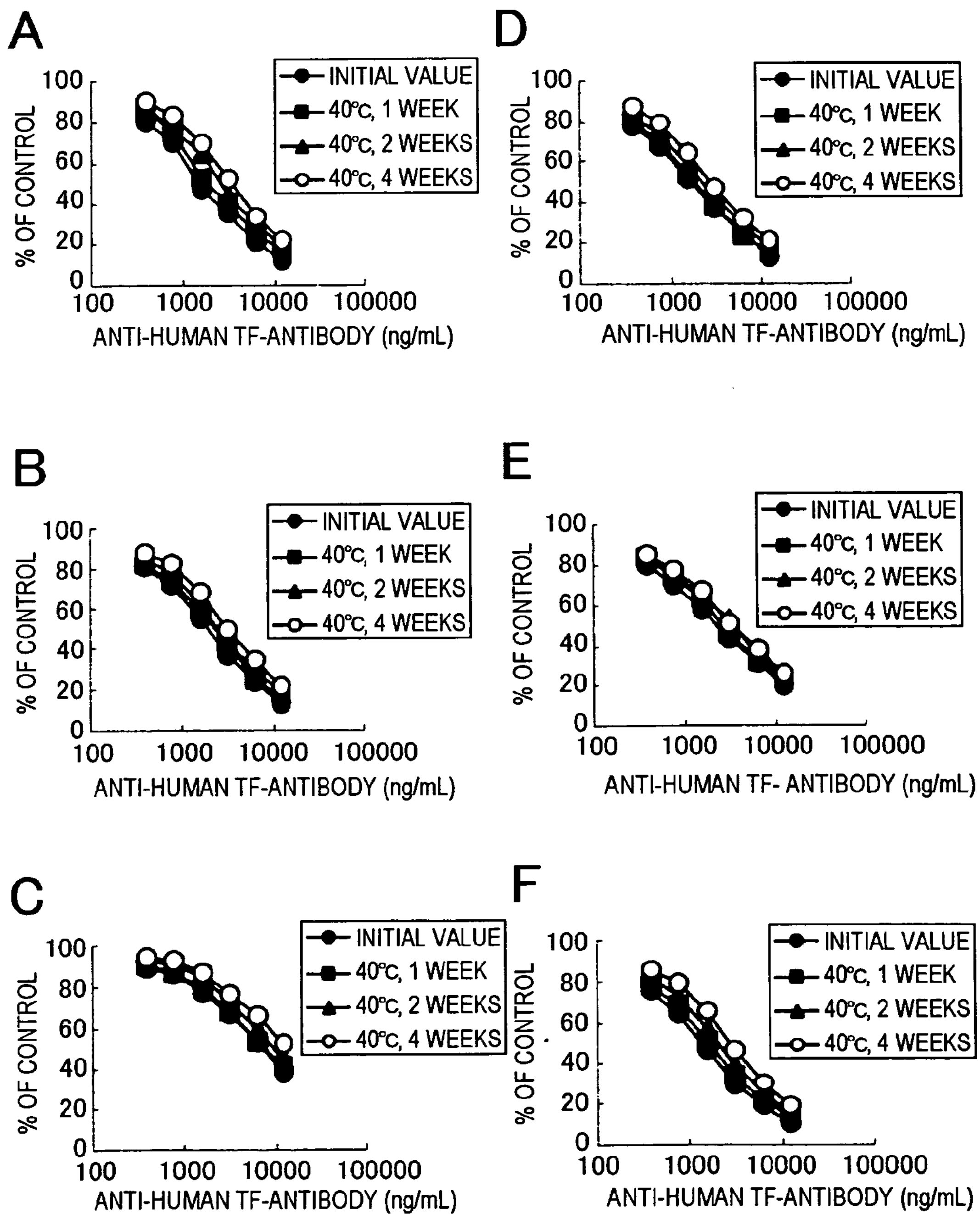
FIG. 15 depicts the anion chromatograph and neutralizing activity before and after the accelerated testing on each of the anti-human TF mutant antibodies and the bulk anti-human TF antibody (99D01). A: 99D01 (G56G); B: G56L; C: G56I; D: G56F; E: G56E; and F: G56K.

The analysis of deamidation using analytical anion exchange chromatography indicated a significant increase in a peak considered to correspond to the deamidated molecule in 99D01 but almost none in the anti-human TF mutant antibodies (FIG. 14). With respect to changes in TF neutralizing activity over time, 99D01 showed a relatively large reduction in activity (FIG. 15).

These results indicate that deamidation of Asn55 is suppressed by substitution of Gly56, and amino acid substitutions Gly56Leu and Gly56Phe were found to be suitable for suppressing deamidation.

9. TF Neutralizing Activity Before and After Accelerated Testing

Figure 16:
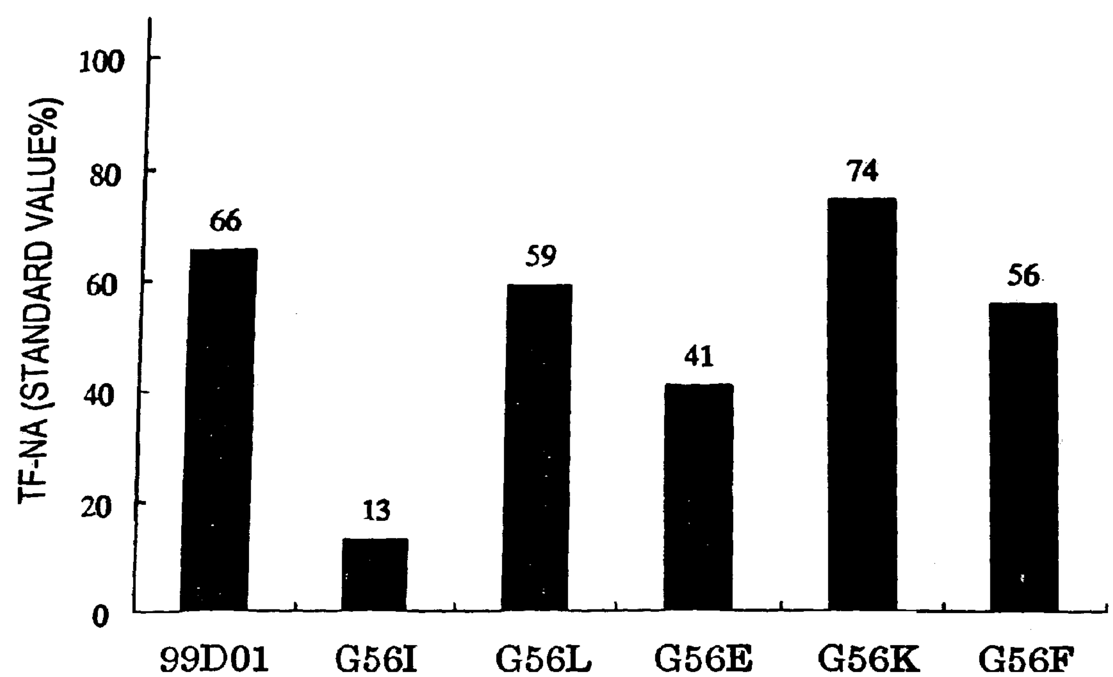
FIG. 16 depicts the neutralizing activity before and after the accelerated testing on each of the anti-human TF mutant antibodies and the bulk anti-human TF antibody (99D01).

TF neutralizing activities of 99D01 and each of the anti-human TF mutant antibodies are shown in FIG. 16. Although Gly56Glu and Gly56Ile showed low activities of about 41% and about 13%, respectively, the other 3 anti-human TF mutant antibodies had activities between 56 to 74%, i.e., nearly the same as 99D01 (66%).

Figure 17:
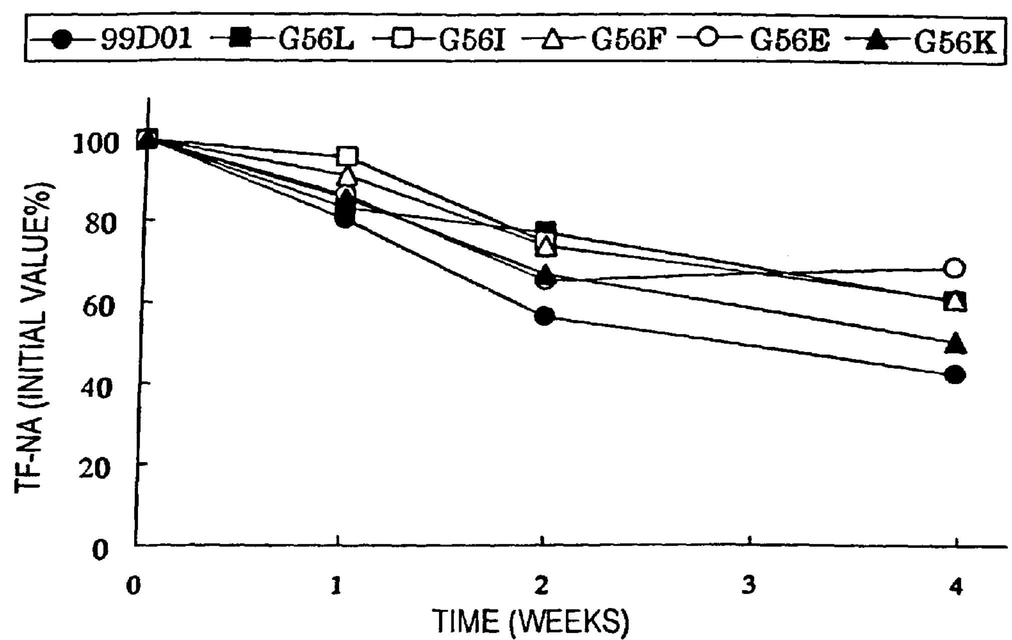
FIG. 17 depicts the neutralizing activity before and after the accelerated testing on each of the anti-human TF mutant antibodies and the bulk anti-human TF antibody (99D01).

The IC50 value compared to the initial value of each sample was calculated from FIG. 15 in order to examine the amount of activity decrease over time of 99D01 and each of the anti-human TF mutant antibodies in the accelerated testing (FIG. 17). Since the IC50 value after the accelerated testing at 40° C. for 4 weeks could not be calculated for the Gly56Ile sample, the results up to 2 weeks are indicated for this sample. The TF neutralizing activity of 99D01 after the accelerated testing at 40° C. for 4 weeks decreased to about 40% of the initial value. On the other hand, each of the mutants in which Gly56 was substituted with another amino acid maintained a TF neutralizing activity of 50 to 70% of the initial value even after the accelerated testing at 40° C. for 4 weeks.

These results indicate that substitution of a glycine that is located adjacent to an asparagine with another amino acid in an antibody does not decrease the antibody activity, yet it suppresses instability due to deamidation.

INDUSTRIAL APPLICABILITY

The present inventors found that substitution of glycine that is located adjacent to asparagine with another amino acid does not influence the antibody activity. The present invention can be applied to produce antibodies little decrease in activity, and thus to obtain antibodies that can be used as pharmaceutical agents that are required to be stable for a long time. Furthermore, the present invention can also be applied to proteins other than antibodies, and is expected to achieve suppression of deamidation without affecting the protein activity.

The invention claimed is:

1. A method for generating a nucleic acid encoding a mutant antibody, the method comprising:

(a) identifying an antibody that is susceptible to deamidation, wherein the antibody includes a first region that is a complementarity determining region (CDR);

(b) identifying an asparagine residue susceptible to deamidation within the first region;

(c) identifying a glycine residue located adjacent and C-terminal to the asparagine residue; and (d) producing a recombinant nucleic acid molecule that encodes a mutant antibody, wherein the mutant antibody is identical to the antibody of (a) except for an alteration selected from the group consisting of (i) a deletion of the glycine residue, and (ii) a substitution of the glycine residue with an amino acid residue other than valine, isoleucine or proline, wherein the mutant antibody of (d) is less susceptible to deamidation than is the antibody of (a), and wherein the mutant antibody of (d) exhibits at least 70% of the antigen binding activity exhibited by the antibody of (a).

2. The method of claim 1, wherein the mutant antibody is a humanized antibody.

3. The method of claim 1, wherein the CDR is CDR2.

4. A method for generating a mutant antibody, the method comprising providing a host cell harboring a recombinant nucleic acid produced by the method of claim 1, and expressing the mutant antibody in the host cell.

5. The method of claim 4, further comprising the step of formulating the mutant antibody into a pharmaceutical composition.

6. The method of claim 1, further comprising:

(e) expressing the mutant antibody encoded by the recombinant nucleic acid of (d); and (f) comparing the antigen binding activity of the antibody of (a) with the antigen binding activity of the mutant antibody of (e).

7. The method of claim 6, further comprising:

(g) comparing the stability over time of the antibody of (a) to the stability of the mutant antibody of (e).

8. The method of claim 1, further comprising:

(e) expressing the mutant antibody encoded by the recombinant nucleic acid of (d); and (f) comparing the stability over time of the antibody of (a) to the stability of the mutant antibody of (e).

9. The method of claim 1, wherein the mutant antibody of (d) exhibits at least 80% of the antigen binding activity exhibited by the antibody of (a).

10. The method of claim 1, wherein the mutant antibody of (d) exhibits at least 90% of the antigen binding activity exhibited by the antibody of (a).

* * * * *

```
SEQUENCE LISTING

<160> NUMBER OF SEQ ID NOS: 28

<210> SEQ ID NO 1
<211> LENGTH: 14
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 1

aattggaagc ttgc                                                  14


<210> SEQ ID NO 2
<211> LENGTH: 14
<212> TYPE: DNA
<213> ORGANISM: Artificial Sequence
<220> FEATURE:
<223> OTHER INFORMATION: Description of Artificial Sequence:an
```

artificially synthesized primer sequence

<400> SEQUENCE: 2
ccttcgaacg ttaa 14

<210> SEQ ID NO 3
<211> LENGTH: 41
<212> TYPE: DNA
<213> ORGANISM: Artificial Sequence
<220> FEATURE:
<223> OTHER INFORMATION: Description of Artificial Sequence:an artificially synthesized primer sequence

<400> SEQUENCE: 3
gagtctagaa tggattggtg ggaatgatcc tgcgaatatg c 41

<210> SEQ ID NO 4
<211> LENGTH: 40
<212> TYPE: DNA
<213> ORGANISM: Artificial Sequence
<220> FEATURE:
<223> OTHER INFORMATION: Description of Artificial Sequence:an artificially synthesized primer sequence

<400> SEQUENCE: 4
gagaatttcg ggtcatacat actatgcata ttcgcaggat 40

<210> SEQ ID NO 5
<211> LENGTH: 43
<212> TYPE: DNA
<213> ORGANISM: Artificial Sequence
<220> FEATURE:
<223> OTHER INFORMATION: Description of Artificial Sequence:an artificially synthesized primer sequence

<400> SEQUENCE: 5
gagtctagaa tggattggtg ggaatgatcc tgcgaataag cat 43

<210> SEQ ID NO 6
<211> LENGTH: 40
<212> TYPE: DNA
<213> ORGANISM: Artificial Sequence
<220> FEATURE:
<223> OTHER INFORMATION: Description of Artificial Sequence:an artificially synthesized primer sequence

<400> SEQUENCE: 6
gagaatttcg ggtcatacat actatgctta ttcgcaggat 40

<210> SEQ ID NO 7
<211> LENGTH: 43
<212> TYPE: DNA
<213> ORGANISM: Artificial Sequence
<220> FEATURE:
<223> OTHER INFORMATION: Description of Artificial Sequence:an artificially synthesized primer sequence

<400> SEQUENCE: 7
gagtctagaa tggattggtg ggaatgatcc tgcgaattgg cat 43

<210> SEQ ID NO 8
<211> LENGTH: 40
<212> TYPE: DNA
<213> ORGANISM: Artificial Sequence
<220> FEATURE:
<223> OTHER INFORMATION: Description of Artificial Sequence:an artificially synthesized primer sequence

```
<400> SEQUENCE: 8

gagaatttcg ggtcatacat actatgccaa ttcgcaggat                        40


<210> SEQ ID NO 9
<211> LENGTH: 43
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 9

gagtctagaa tggattggtg ggaatgatcc tgcgaatcag cat                    43


<210> SEQ ID NO 10
<211> LENGTH: 40
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 10

gagaatttcg ggtcatacat actatgctga ttcgcaggat                        40


<210> SEQ ID NO 11
<211> LENGTH: 43
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 11

gagtctagaa tggattggtg ggaatgatcc tgcgaatgag cat                    43


<210> SEQ ID NO 12
<211> LENGTH: 40
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 12

gagaatttcg ggtcatacat actatgctca ttcgcaggat                        40


<210> SEQ ID NO 13
<211> LENGTH: 43
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 13

gagtctagaa tggattggtg ggaatgatcc tgcgaatttc cat                    43


<210> SEQ ID NO 14
<211> LENGTH: 40
<212> TYPE: DNA
<213> ORGANISM: Artificial Sequence
<220> FEATURE:
<223> OTHER INFORMATION: Description of Artificial Sequence:an
      artificially synthesized primer sequence

<400> SEQUENCE: 14
```

gagaatttcg ggtcatacat actatggaaa ttcgcaggat 40

<210> SEQ ID NO 15
<211> LENGTH: 43
<212> TYPE: DNA
<213> ORGANISM: Artificial Sequence
<220> FEATURE:
<223> OTHER INFORMATION: Description of Artificial Sequence:an artificially synthesized primer sequence

<400> SEQUENCE: 15
gagtctagaa tggattggtg ggaatgatcc tgcgaatacc cat 43

<210> SEQ ID NO 16
<211> LENGTH: 40
<212> TYPE: DNA
<213> ORGANISM: Artificial Sequence
<220> FEATURE:
<223> OTHER INFORMATION: Description of Artificial Sequence:an artificially synthesized primer sequence

<400> SEQUENCE: 16
gagaatttcg ggtcatacat actatgggta ttcgcaggat 40

<210> SEQ ID NO 17
<211> LENGTH: 43
<212> TYPE: DNA
<213> ORGANISM: Artificial Sequence
<220> FEATURE:
<223> OTHER INFORMATION: Description of Artificial Sequence:an artificially synthesized primer sequence

<400> SEQUENCE: 17
gagtctagaa tggattggtg ggaatgatcc tgcgaataac cat 43

<210> SEQ ID NO 18
<211> LENGTH: 40
<212> TYPE: DNA
<213> ORGANISM: Artificial Sequence
<220> FEATURE:
<223> OTHER INFORMATION: Description of Artificial Sequence:an artificially synthesized primer sequence

<400> SEQUENCE: 18
gagaatttcg ggtcatacat actatggtta ttcgcaggat 40

<210> SEQ ID NO 19
<211> LENGTH: 43
<212> TYPE: DNA
<213> ORGANISM: Artificial Sequence
<220> FEATURE:
<223> OTHER INFORMATION: Description of Artificial Sequence:an artificially synthesized primer sequence

<400> SEQUENCE: 19
gagtctagaa tggattggtg ggaatgatcc tgcgaatgac cat 43

<210> SEQ ID NO 20
<211> LENGTH: 40
<212> TYPE: DNA
<213> ORGANISM: Artificial Sequence
<220> FEATURE:
<223> OTHER INFORMATION: Description of Artificial Sequence:an artificially synthesized primer sequence

<400> SEQUENCE: 20
gagaatttcg ggtcatacat actatggtca ttcgcaggat 40

<210> SEQ ID NO 21
<211> LENGTH: 43
<212> TYPE: DNA
<213> ORGANISM: Artificial Sequence
<220> FEATURE:
<223> OTHER INFORMATION: Description of Artificial Sequence:an artificially synthesized primer sequence

<400> SEQUENCE: 21
gagtctagaa tggattggtg ggaatgatcc tgcgaatccc cat 43

<210> SEQ ID NO 22
<211> LENGTH: 40
<212> TYPE: DNA
<213> ORGANISM: Artificial Sequence
<220> FEATURE:
<223> OTHER INFORMATION: Description of Artificial Sequence:an artificially synthesized primer sequence

<400> SEQUENCE: 22
gagaatttcg ggtcatacat actatgggga ttcgcaggat 40

<210> SEQ ID NO 23
<211> LENGTH: 43
<212> TYPE: DNA
<213> ORGANISM: Artificial Sequence
<220> FEATURE:
<223> OTHER INFORMATION: Description of Artificial Sequence:an artificially synthesized primer sequence

<400> SEQUENCE: 23
gagtctagaa tggattggtg ggaatgatcc tgcgaattgc cat 43

<210> SEQ ID NO 24
<211> LENGTH: 40
<212> TYPE: DNA
<213> ORGANISM: Artificial Sequence
<220> FEATURE:
<223> OTHER INFORMATION: Description of Artificial Sequence:an artificially synthesized primer sequence

<400> SEQUENCE: 24
gagaatttcg ggtcatacat actatggcaa ttcgcaggat 40

<210> SEQ ID NO 25
<211> LENGTH: 444
<212> TYPE: PRT
<213> ORGANISM: Homo sapiens

<400> SEQUENCE: 25

```
Gln Val Gln Leu Leu Glu Ser Gly Ala Val Leu Ala Arg Pro Gly Thr
  1               5                  10                  15

Ser Val Lys Ile Ser Cys Lys Ala Ser Gly Phe Asn Ile Lys Asp Tyr
             20                  25                  30

Tyr Met His Trp Val Lys Gln Arg Pro Gly Gln Gly Leu Glu Trp Ile
         35                  40                  45

Gly Gly Asn Asp Pro Ala Asn Gly His Ser Met Tyr Asp Pro Lys Phe
     50                  55                  60

Gln Gly Arg Val Thr Ile Thr Ala Asp Thr Ser Thr Ser Thr Val Phe
 65                  70                  75                  80

Met Glu Leu Ser Ser Leu Arg Ser Glu Asp Thr Ala Val Tyr Tyr Cys
                 85                  90                  95

Ala Arg Asp Ser Gly Tyr Ala Met Asp Tyr Trp Gly Gln Gly Thr Leu
            100                 105                 110
```

```
Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440


<210> SEQ ID NO 26
<211> LENGTH: 214
<212> TYPE: PRT
<213> ORGANISM: Homo sapiens

<400> SEQUENCE: 26

Asp Ile Gln Met Thr Gln Ser Pro Ser Ser Leu Ser Ala Ser Val Gly
  1               5                  10                  15

Asp Arg Val Thr Ile Thr Cys Lys Ala Ser Gln Asp Ile Lys Ser Phe
            20                  25                  30

Leu Ser Trp Tyr Gln Gln Lys Pro Glu Lys Ala Pro Lys Ser Leu Ile
        35                  40                  45
```

```
Tyr Tyr Ala Thr Ser Leu Ala Asp Gly Val Pro Ser Arg Phe Ser Gly
     50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Leu Gln His Gly Glu Ser Pro Tyr
                 85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 27
<211> LENGTH: 37
<212> TYPE: DNA
<213> ORGANISM: Artificial Sequence
<220> FEATURE:
<223> OTHER INFORMATION: Description of Artificial Sequence:an
      artificially synthesized sequence

<400> SEQUENCE: 27

gagtctagaa tggattggtg ggaatgatcc tgcgaat                              37


<210> SEQ ID NO 28
<211> LENGTH: 39
<212> TYPE: DNA
<213> ORGANISM: Artificial Sequence
<220> FEATURE:
<223> OTHER INFORMATION: Description of Artificial Sequence:an
      artificially synthesized sequence
<220> FEATURE:
<221> NAME/KEY: misc_feature
<222> LOCATION: (1)..(2)
<223> OTHER INFORMATION: n = g, a, c, or t

<400> SEQUENCE: 28

nnattcgcag gatcattccc accaatccat tctagactc                            39
```